(12) United States Patent
Pierobon et al.

(10) Patent No.: US 8,652,456 B2
(45) Date of Patent: Feb. 18, 2014

(54) AQUEOUS PREPARATIONS COMPRISING AT LEAST ONE WATER-SOLUBLE OR WATER-DISPERSIBLE COPOLYMER WITH CATIONGENIC GROUPS

(75) Inventors: Marianna Pierobon, Ludwigshafen (DE); Son Nguyen-Kim, Hemsbach (DE); Peter Hossel, Schifferstadt (DE)

(73) Assignee: BASF SE, Ludwigshafen (DE)

( * ) Notice: Subject to any disclaimer, the term of this patent is extended or adjusted under 35 U.S.C. 154(b) by 1424 days.

(21) Appl. No.: 11/629,885

(22) PCT Filed: Jun. 15, 2005

(86) PCT No.: PCT/EP2005/006401
§ 371 (c)(1),
(2), (4) Date: Dec. 18, 2006

(87) PCT Pub. No.: WO2005/123014
PCT Pub. Date: Dec. 29, 2005

(65) Prior Publication Data
US 2008/0075689 A1    Mar. 27, 2008

(30) Foreign Application Priority Data

Jun. 21, 2004 (DE) .......................... 102004029773
Feb. 28, 2005 (DE) .......................... 102005009668
Mar. 2, 2005 (DE) .......................... 102005010108

(51) Int. Cl.
*A61K 31/74* (2006.01)
*A61K 47/48* (2006.01)

(52) U.S. Cl.
USPC ........................ 424/78.27; 525/54.1

(58) Field of Classification Search
USPC ........................ 424/78.27; 525/54.1
See application file for complete search history.

(56) References Cited

U.S. PATENT DOCUMENTS

| | | | |
|---|---|---|---|
| 3,405,084 A | | 10/1968 | Bohac et al. |
| 3,953,608 A | * | 4/1976 | Vanlerberghe et al. ....... 514/777 |
| 5,783,601 A | * | 7/1998 | Tanahashi et al. ............ 514/557 |
| 5,840,804 A | | 11/1998 | Carl et al. |
| 5,869,032 A | * | 2/1999 | Tropsch et al. ............ 424/70.15 |
| 5,965,213 A | * | 10/1999 | Sacharski et al. ............. 427/475 |
| 6,191,188 B1 | * | 2/2001 | Hossel et al. ................. 523/105 |
| 6,231,876 B1 | | 5/2001 | Niessner et al. |
| 6,403,542 B1 | | 6/2002 | Maurin et al. |
| 6,932,964 B1 | | 8/2005 | Kim et al. |
| 7,034,068 B1 | | 4/2006 | Negele et al. |
| 2003/0104020 A1 | * | 6/2003 | Davison et al. ............... 424/401 |
| 2003/0147929 A1 | * | 8/2003 | Kim et al. ..................... 424/401 |
| 2005/0175572 A1 | * | 8/2005 | Nguyen-Kim et al. .... 424/70.16 |
| 2006/0116448 A1 | | 6/2006 | Negele et al. |
| 2008/0020004 A1 | | 1/2008 | Birkel et al. |

FOREIGN PATENT DOCUMENTS

| | | | |
|---|---|---|---|
| AU | A 9438198 | | 3/1999 |
| CA | 2484140 | * | 11/2003 |
| DE | 197 38 303 A1 | | 3/1999 |
| DE | 198 38 851 A1 | | 3/2000 |
| DE | 101 51 592 A1 | | 4/2003 |
| DE | 202004002471 U1 | | 4/2004 |
| EP | 0437114 A1 | | 7/1991 |
| EP | 0 670 333 A2 | | 9/1995 |
| EP | 0 929 285 B1 | | 7/1999 |
| EP | 1 302 191 A2 | | 4/2003 |
| WO | WO-94/06409 | | 3/1994 |
| WO | WO-98/14164 | | 4/1998 |
| WO | WO-00/27893 | | 5/2000 |
| WO | WO-03/092640 A2 | | 11/2003 |
| WO | WO03092640 | * | 11/2003 |
| WO | WO-2004/030642 A1 | | 4/2004 |

OTHER PUBLICATIONS

Laba, Rheological Properties of Cosmetics and Toiletries, Cosmetic Science and Technology Series/vol. 13, ISBN-10: 0824790901, Sep. 16, 1993, p. 96-98.*
R. Lochhead. "The History of Polymers in Hair Care". *Cosmetics & Toiletries*, vol. 103, Dec. 1998 pp. 23-61.
Ross et al. "Indicator Reagents". *Ullmann's Encyclopedia of Industrial Chemistry*, 6. Auflage, vol. 17, pp. 645-655.
International Search Report for PCT/EP2005/006401, mailed Oct. 21, 2005.
International Preliminary Report on Patentability for International Application PCT/EP2005/006401, dated Oct. 5, 2006.

* cited by examiner

*Primary Examiner* — Blessing M Fubara
*Assistant Examiner* — Jennifer A Berrios
(74) *Attorney, Agent, or Firm* — Novak Druce Connolly Bove + Quigg LLP

(57) ABSTRACT

The present invention relates to aqueous preparations comprising at least one water-soluble or water-dispersible copolymer with cationogenic groups which comprises at least one monomer with at least one protonatable nitrogen atom and at least one further monomer copolymerizable therewith in copolymerized form, and at least one cosmetically acceptable carrier, where the pH of the aqueous preparation has a value in the range from pH 4 to pH 6.

16 Claims, No Drawings

AQUEOUS PREPARATIONS COMPRISING AT LEAST ONE WATER-SOLUBLE OR WATER-DISPERSIBLE COPOLYMER WITH CATIONGENIC GROUPS

CROSS REFERENCE TO RELATED APPLICATIONS

This application is a National Stage entry under 35 U.S.C. §371 of PCT/EP2005/006401 filed on Jun. 15, 2005, which claims priority to German Application Nos. 10 2004 029773.8, filed Jun. 21, 2004, and 10 2005 009668.9, filed Feb. 28, 2005, 10 2005 010108.9, filed Mar. 2, 2005. The entire contents of each of the above-applications are incorporated herein by reference.

The present invention relates to aqueous preparations comprising at least one water-soluble or water-dispersible copolymer with cationogenic groups which comprises at least one monomer with at least one protonatable nitrogen atom and at least one further monomer copolymerizable therewith in copolymerized form, and at least one cosmetically acceptable carrier, where the pH of the aqueous preparation has a value in the range from pH 4 to pH 6.

The invention further relates to the use of these aqueous preparations and to methods for their preparation.

Cosmetically and pharmaceutically acceptable water-soluble polymers are used widely in cosmetics and medicine. In soaps, creams and lotions, for example, they are usually used as formulation agents, e.g. as thickener, foam stabilizer or water absorbent, or else to alleviate the irritative effect of other ingredients or to improve the dermal application of active ingredients.

Their task in hair cosmetics is to influence the properties of the hair. In pharmacy, they are used, for example, as coatings or binders for solid drug forms.

For hair cosmetics, film-forming polymers are used, for example, as conditioners in order to improve the dry and wet combability, the feel to the touch, shine and appearance, and to impart antistatic properties to the hair. It is known to use water-soluble polymers with cationic functionalities in hair conditioners which have a greater affinity to the surface of the hair, which is negatively charged as a consequence of its structure, and prevent electrostatic charging of the hair. The structure and mode of action of various hair treatment polymers are described in Cosmetic & Toiletries 103 (1988) 23. Standard commercial cationic conditioning polymers are, for example, cationic hydroxyethylcellulose, cationic polymers based on N-vinylpyrrolidone, e.g. copolymers of N-vinylpyrrolidone and quaternized N-vinylimidazole or copolymers of acrylamide and diallyldimethylammonium chloride.

To set hairstyles, use is made, for example, of vinyllactam homo- and copolymers and polymers containing carboxylate groups. Requirements for hair-setting resins are, for example, strong hold at high atmospheric humidity, elasticity, ability to be washed out of the hair, compatibility in the formulation, lowest possible stickiness of the formed film and a pleasant feel of the hair treated therewith.

It is often problematical to provide products with a complex profile of properties. Thus, there is a need for cosmetic preparations which are capable of forming essentially smooth, nonsticky films which give the hair and the skin good sensorially ascertainable properties, such as a pleasant feel, and at the same time have a good conditioning effect or setting effect.

EP-A-670 333 describes crosslinked water-soluble polymer dispersions which are obtainable by polymerizing a monomer mixture comprising at least one water-soluble monomer, at least one crosslinker, and, if appropriate, hydrophobic and/or amphiphilic monomers in the presence of a polymeric dispersant. Besides a large number of others, water-soluble monomers which may be used are also N-vinylpyrrolidone and monomers with cationic/cationizable groups, such as N-vinylimidazole.

EP-A-929 285 teaches the use of water-soluble copolymers which comprise vinylcarboxamide units and vinylimidazole units in copolymerized form as a constituent of cosmetic compositions.

WO 00/27893 describes aqueous polymer dispersions based on N-vinylcarboxamides and if appropriate comonomers, where N-vinylpyrrolidone, N-vinylimidazole and N-vinylimidazole derivatives are also mentioned besides a large number of others. The polymerization takes place in the presence of at least one polymeric dispersant.

WO 03/92640 relates to cosmetic compositions which comprise at least one water-soluble copolymer which is obtainable by free-radical copolymerization of acrylamide and/or methacrylamide and further water-soluble $\alpha,\beta$-ethylenically unsaturated compounds copolymerizable therewith, if appropriate in the presence of a water-soluble polymeric graft base.

There continues to be a need for improvement in the case of the preparations for cosmetic and pharmaceutical applications known from the prior art. This is true especially for preparations comprising polymers which, besides having good film-forming properties, also permit adjustment of the rheological properties of the products, meaning that they can be formulated, for example, in the form of mousses, foams or gels.

It was an object of the present invention to find a cosmetic preparation suitable in particular for mousse and foam applications having improved setting properties which are additionally notable for producing elastic hairstyles coupled with simultaneously strong hold even at high atmospheric humidity, and is further characterized by good ability to be washed out, lowest possible stickiness and good feel of the hair treated therewith.

This object is achieved by aqueous preparations comprising at least one water-soluble or water-dispersible copolymer with cationogenic groups which comprises at least one monomer with at least one protonatable nitrogen atom and at least one further monomer copolymerizable therewith in copolymerized form, and at least one cosmetically acceptable carrier, where the pH of the aqueous preparations has a value in the range from pH 4 to pH 6.

The invention therefore provides aqueous preparations comprising

A) at least one water-soluble or water-dispersible copolymer A) with cationogenic groups which comprises
   a) at least one monomer with at least one protonatable nitrogen atom and
   b) at least one further monomer copolymerizable therewith in copolymerized form, and
B) at least one cosmetically acceptable carrier, where the pH of the aqueous preparation has a value in the range from pH 4 to pH 6.

For the purposes of this invention, protonatable nitrogen atoms are those nitrogen atoms which can be converted into the cationic charge state by protonation, preferably with the help of acids.

Adjustment of the pH

The pH is a term introduced by Sørensen for the negative $\log_{10}$ of the concentration of the hydrogen ions $c(H^+)$ in mol/l in aqueous solution.

The pH of water (neutral pH range) is 7.0 at 22° C. The pH is temperature-dependent and decreases at higher temperatures. The pH is determined by means of potentiometric measurements known to the person skilled in the art using pH electrodes (glass electrodes) or calorimetrically using indicator dyes (pH paper, litmus paper, pH sticks). Examples of indicators are given in Ullmann's Encyclopedia of Industrial Chemistry, 6th edition, Vol. 17, pages 645 to 655. To determine the pH using electrodes, all commercially available pH meters can be used.

The pH of the preparations according to the invention is determined by an abovementioned method known to the person skilled in the art at temperatures of from 20 to 25° C.

According to the invention, the pH of the aqueous preparation has a value in the range from pH 4 to pH 6. Preferably, this pH is adjusted by adding a Brönsted acid. Preferred Brönsted acids are water-soluble organic and inorganic acids.

Possible organic acids may be mono- and polybasic, optionally substituted aliphatic and aromatic carboxylic acids, mono- and polybasic, optionally substituted aliphatic and aromatic sulfonic acids or mono- and polybasic, optionally substituted aliphatic and aromatic phosphonic acids.

Preferred organic acids are hydroxycarboxylic acids, i.e. derivatives of carboxylic acids in which one or more H atoms are replaced by hydroxyl groups.

Examples of hydroxycarboxylic acids which may be mentioned are glycolic acid, lactic acid, tartaric acid and citric acid.

Accordingly, preference is given to adjusting the pH of the preparations by adding a hydroxy acid, with lactic acid being particularly preferred.

Preferred inorganic acids which may be mentioned are phosphoric acid, phosphorous acid, sulfuric acid, sulfurous acid and hydrochloric acid.

In a preferred embodiment, the pH of the aqueous preparations has a value of at least 4.5, preferably 5, particularly preferably 5.2, in particular 5.4 and a value of at most 6, preferably 5.8, in particular 5.6. According to the invention, however, the pH can preferably also have values of 5.1, 5.3, 5.5, 5.7 or 5.9.

According to the invention, the pH of the preparations is preferably adjusted at a time when the preparation of component A, i.e. the polymerization, is complete.

The preparation of component A is regarded as being complete when the content of unreacted monomers in the preparation is less than 5, preferably less than 2, particularly preferably less than 0.1, very particularly preferably less than 0.05, based on the total mass of component A.

According to the invention, the pH of the preparations can be adjusted at any time after the preparation of component A is complete.

In addition to the adjustment according to the invention of the pH of the aqueous preparation after the preparation of component A is complete, the pH of the monomer solutions can also be adjusted to values in the range from pH 6 to pH 7 before or during the preparation of component A.

Accordingly, it may also be advantageous to adjust the pH of the monomer seeds before or during the polymerization to a value in the range from pH 6 to pH 7 and to adjust the pH of the aqueous preparation when polymerization is complete in accordance with the invention to a value of from pH 4 to pH 6.

Accordingly, the invention further provides a method of preparing the preparation according to the invention, wherein the pH adjustment to a value in the range from 4 to 6 takes place after the preparation of component A) is complete.

In a particularly preferred embodiment, the pH of the preparation is then adjusted when the preparation is already in its application form, for example in the form of a gel, foam, spray, ointment, cream, emulsion, suspension, lotion, milk or paste preparation.

According to the invention, the pH adjustment thus preferably takes place on cosmetically acceptable gel, foam, spray, ointment, cream, emulsion, suspension, lotion, milk or paste preparations.

For the purposes of the present invention, the expression "alkyl" includes straight-chain and branched alkyl groups. Short-chain alkyl groups suitable according to the invention are, for example, straight-chain or branched $C_1$-$C_7$-alkyl, preferably $C_1$-$C_6$-alkyl and particularly preferably $C_1$-$C_4$-alkyl groups. These include, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl etc.

Suitable longer-chain $C_8$-$C_{30}$-alkyl and $C_8$-$C_{30}$-alkenyl groups are straight-chain and branched alkyl and alkenyl groups. These are preferably predominantly linear alkyl radicals, as also arise in natural or synthetic fatty acids and fatty alcohols and oxo alcohols, which may, if appropriate, additionally be mono-, di- or polyunsaturated. These include, for example, n-hexyl(ene), n-heptyl(ene), n-octyl(ene), n-nonyl(ene), n-decyl(ene), n-undecyl(ene), n-dodecyl(ene), n-tridecyl(ene), n-tetradecyl(ene), n-pentadecyl(ene), n-hexadecyl(ene), n-heptadecyl(ene), n-octadecyl(ene), n-nonadecyl(ene) etc.

Cycloalkyl is preferably $C_5$-$C_8$-cycloalkyl, such as cyclopentyl, cyclohexyl, cycloheptyl or cyclooctyl.

Aryl includes unsubstituted and substituted aryl groups and is preferably phenyl, tolyl, xylyl, mesityl, naphthyl, fluorenyl, anthracenyl, phenanthrenyl, naphthacenyl and in particular phenyl, tolyl, xylyl or mesityl.

In the text below, compounds which can be derived from acrylic acid and methacrylic acid are sometimes referred to in short by adding the syllable "(meth)" to the compound derived from acrylic acid.

The preparations according to the invention can be formulated advantageously as foam under normal conditions.

For the purposes of the present invention, water-soluble monomers and polymers are understood as meaning monomers and polymers which dissolve in water in an amount of at least 1 g/l at 20° C.

Water-dispersible monomers and polymers are understood as meaning monomers and polymers which disintegrate into dispersible particles under the application of shear forces, for example by stirring.

Hydrophilic monomers are preferably water-soluble or at least water-dispersible.

To prepare the copolymers A), use is made of monomers with at least one protonatable nitrogen atom, in particular N-vinylimidazole and/or derivatives thereof and amides of $\alpha,\beta$-ethylenically unsaturated mono- and dicarboxylic acids with diamines which have at least one primary or secondary amino group. In a preferred embodiment of the invention, the copolymer A) accordingly comprises at least one monomer with at least one protonatable nitrogen atom chosen from N-vinylimidazole and/or a derivative thereof and amides of $\alpha,\beta$-ethylenically unsaturated mono- and dicarboxylic acids with diamines which have at least one primary or secondary amino group, in nonquaternized form.

In this connection, "quaternized form" is understood as meaning the cationic charge state of the nitrogen atom which is produced, for example, by alkylation, but not by protonation.

It is also possible, for the preparation of the copolymers A), to use further charged N-vinylimidazole (derivatives) different from uncharged N-vinylimidazole (derivatives). Furthermore, it is possible to use further cationogenic and/or cationic monomers different from N-vinylimidazole (derivatives) (i.e. further monomers in un-, partially or completely protonated and/or quaternized form).

Preferably, the copolymers A) comprise no monomers with anionogenic and/or anionic groups in copolymerized form.

Monomer a)

The copolymer A) used in the preparations according to the invention preferably comprises 0.5 to 40% by weight, particularly preferably 1 to 30% by weight, very particularly preferably 3 to 20% by weight, and in particular 3 to 15% by weight, based on the total weight of the monomers used for the polymerization, of at least one monomer a) in copolymerized form. In a particular embodiment, the content of monomers a) is at most 25% by weight.

The copolymer A) used in the preparations according to the invention comprises at least one monomer with at least one protonatable nitrogen atom in copolymerized form.

Preferred monomers with at least one protonatable nitrogen atom are N-vinylimidazole compounds of the general formula (I). Particularly preferably, the copolymer A) accordingly comprises, as monomer a), at least one N-vinylimidazole compound of the general formula (I)

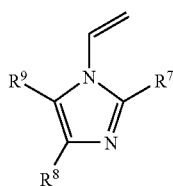

(I)

in copolymerized form, in which $R^7$ to $R^9$, independently of one another, are hydrogen, $C_1$-$C_4$-alkyl or phenyl.

Examples of compounds of the general formula (I) are given in Table 1 below:

TABLE 1

| $R^7$ | $R^8$ | $R^9$ |
|---|---|---|
| H | H | H |
| Me | H | H |
| H | Me | H |
| H | H | Me |
| Me | Me | H |
| H | Me | Me |
| Me | H | Me |
| Ph | H | H |
| H | Ph | H |
| H | H | Ph |
| Ph | Me | H |
| Ph | H | Me |
| Me | Ph | H |
| H | Ph | Me |
| H | Me | Ph |
| Me | H | Ph |

Me = methyl
Ph = phenyl

A very particularly preferred monomer a) is 1-vinylimidazole (N-vinylimidazole).

In addition, protonatable monomers a) which can be used are aminoalkyl acrylates and methacrylates and aminoalkylacrylamides and methacrylamides of the general formula (II)

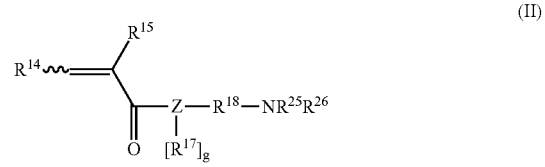

(II)

where $R^{14}$ and $R^{15}$; independently of one another, are chosen from the group consisting of hydrogen, $C_1$-$C_8$ linear- or branched-chain alkyl, methoxy, ethoxy, 2-hydroxyethoxy, 2-methoxyethoxy and 2-ethoxyethyl. Preference is given to hydrogen, methyl or ethyl, $R^{17}$ is hydrogen or methyl, $R^{18}$ is alkylene or hydroxyalkylene with 1 to 24 carbon atoms, optionally substituted by alkyl, preferably $C_2H_4$, $C_3H_6$, $C_4H_8$, $CH_2$—$CH(OH)$—$CH_2$, g is 0 or 1, Z is nitrogen when g=1 or oxygen when g=0, $R^{25}$ and $R^{26}$ are in each case and independently of one another chosen from the group consisting of hydrogen, $C_1$-$C_{40}$ linear- or branched-chain alkyl, formyl, $C_1$-$C_{10}$ linear- or branched-chain acyl, N,N-dimethylaminoethyl, 2-hydroxyethyl, 2-methoxyethyl, 2-ethoxyethyl, hydroxypropyl, methoxypropyl, ethoxypropyl or benzyl. Preference is given to hydrogen, methyl, ethyl, n-propyl and benzyl.

The amides may be present unsubstituted, N-alkyl- or N-alkylamino-monosubstituted or N,N-dialkyl-substituted or N,N-dialkylamino-disubstituted in which the alkyl or alkylamino groups are derived from $C_1$-$C_{40}$ linear, $C_3$-$C_{40}$ branched-chain or $C_3$-$C_{40}$ carbocyclic units.

Preferred protonatable comonomers a) of the formula (II) are N,N-dimethylaminomethyl(meth)acrylate, N,N-diethylaminomethyl(meth)acrylate, N,N-dimethylaminoethyl (meth)acrylate, N,N-diethylaminoethyl(meth)acrylate, N,N-dimethylaminobutyl(meth)acrylate, N,N-diethylaminobutyl (meth)acrylate, N,N-dimethylaminohexyl(meth)acrylate, N,N-dimethylaminooctyl(meth)acrylate, N,N-dimethylaminododecyl(meth)acrylate.

Preference is also given to N-[2-(dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)butyl]methacrylamide, N-[2-(diethylamino)ethyl]acrylamide, N-[4-(dimethylamino)cyclohexyl]acrylamide, N-[4-(dimethylamino)cyclohexyl]methacrylamide, N-[8-(dimethylamino)octyl]methacrylamide, N-[12-(dimethylamino)dodecyl]methacrylamide, N-[3-(diethylamino)propyl]methacrylamide and N-[3-(diethylamino)propyl]acrylamide. Very particular preference is given to N,N-dimethylaminoethylmethacrylate, N-[3-(dimethylamino)propyl]methacrylamide, N-methylaminoethylmethacrylate, N-[3-(methylamino)propyl]methacrylamide, aminoethylmethacrylate and N-[3-aminopropyl] methacrylamide.

In particular, preference is given to N-[3-(dimethylamino)propyl]methacrylamide.

In addition, the protonatable monomer a) can also be chosen from diallylamines of the general formula (III)

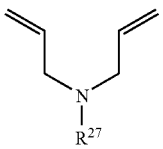
(III)

where $R^{27}$ is hydrogen or $C_1$ to $C_{24}$ alkyl. Particular preference is given to N,N-diallylamine and N,N-diallyl-N-methylamine, in particular N,N-diallyl-N-methylamine.

In addition, the monomer a) can be chosen from compounds such as 1,3-divinylimidazolid-2-one or N-disubstituted vinylamines of the general formula (IV):

where
$R^{14}$ and $R^{15}$, independently of one another, are chosen from the group consisting of hydrogen, $C_1$-$C_8$ linear- or branched-chain alkyl, methoxy, ethoxy, 2-hydroxyethoxy, 2-methoxyethoxy and 2-ethoxyethyl. Preference is given to hydrogen, methyl or ethyl, n is 0, 1 or 2, and $R^{28}$ is chosen from the group consisting of hydrogen, $C_1$-$C_{40}$ linear- or branched-chain alkyl radicals, formyl, $C_1$-$C_{10}$ linear- or branched-chain acyl, N,N-dimethylaminoethyl, 2-hydroxyethyl, 2-methoxyethyl, 2-ethoxyethyl, hydroxypropyl, methoxypropyl, ethoxypropyl or benzyl, preferably methyl, ethyl, n-propyl and benzyl. If n=0, then both radicals $R^{28}$ should not be hydrogen at the same time.

Monomer b)

The copolymer A) used in the preparations according to the invention preferably comprises 20 to 99.5% by weight, particularly preferably 20 to 70% by weight, in particular 30 to 70% by weight, based on the total weight of the monomers used for the polymerization, of at least one further monomer b) copolymerizable therewith in copolymerized form. In a particular embodiment, the content of monomers b) is at least 50% by weight.

Monomer b1)

Preferably, the copolymer A) additionally comprises at least one N-vinyllactam b1) in copolymerized form. Suitable monomers b1) are unsubstituted N-vinyllactams and N-vinyllactam derivatives which can, for example, have one or more $C_1$-$C_6$-alkyl substituents, such as methyl, ethyl, n-propyl, isopropyl, n-butyl, sec-butyl, tert-butyl etc. These include, for example, N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam etc. and mixtures thereof.

Preference is given to using N-vinylpyrrolidone, N-vinylcaprolactam or mixtures thereof.

In a particular embodiment, the preparations according to the invention comprise, as component A), a copolymer which consists only of monomer units of the abovementioned monomers a) and b1).

Preferably, these copolymers A) then comprise 0.5 to 40% by weight, particularly preferably 1 to 30% by weight, in particular 3 to 20% by weight, of at least one monomer a) in copolymerized form. Accordingly, these copolymers A) preferably comprise 60 to 99.5% by weight, particularly preferably 70 to 99% by weight, in particular 80 to 97% by weight of at least one monomer b) in copolymerized form.

In a preferred embodiment, the preparations according to the invention comprise, as component A), a copolymer which, in addition to the abovementioned monomers a) and b1), comprises at least one further monomer b2) different therefrom in copolymerized form.

Monomer b2)

The copolymers A) can additionally comprise at least one nonionic water-soluble monomer b2) which is different from the components a) and b1) and copolymerizable therewith.

Preferably, the content of monomers b2) is 0 to 50% by weight, particularly preferably 5 to 50% by weight, in particular 10 to 40% by weight, based on the total weight of the monomers used for the polymerization.

Preferably, the component b2) is chosen from b2.1) N-vinylamides of saturated $C_1$-$C_8$-monocarboxylic acids, b2.2) primary amides of α,β-ethylenically unsaturated monocarboxylic acids and their N-alkyl and N,N-dialkyl derivatives which, in addition to the carbonyl carbon atom of the amide group, have at most 8 further carbon atoms, b2.3) esters of α,β-ethylenically unsaturated mono- and dicarboxylic acids with diols, b2.4) amides of α,β-ethylenically unsaturated mono- and dicarboxylic acids with aminoalcohols which have a primary or secondary amino group, b2.5) polyether acrylates and mixtures thereof.

Open-chain N-vinylamide compounds suitable as monomers b2.1) are, for example, N-vinylformamide, N-vinyl-N-methylformamide, N-vinylacetamide, N-vinyl-N-methylacetamide, N-vinyl-N-ethylacetamide, N-vinylpropionamide, N-vinyl-N-methylpropionamide and N-vinylbutyramide.

Suitable monomers b2.2) are, for example, acrylamide, methacrylamide, N-methyl(meth)acrylamide, N-ethyl(meth)acrylamide, N-propyl(meth)acrylamide, N-(n-butyl)(meth)acrylamide, N-(tert-butyl)(meth)acrylamide, N,N-dimethyl(meth)acrylamide, N,N-diethyl(meth)acrylamide, piperidinyl(meth)acrylamide and morpholinyl(meth)acrylamide, where (meth)acrylamide is preferred and methacrylamide is particularly preferred.

Suitable monomers b2.3) are, for example, 2-hydroxyethyl acrylate, 2-hydroxyethyl methacrylate, 2-hydroxyethyl ethacrylate, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate and 3-hydroxy-2-ethylhexyl methacrylate.

Suitable monomers b2.4) are, for example, 2-hydroxyethylacrylamide, 2-hydroxyethylmethacrylamide, 2-hydroxyethylethacrylamide, 2-hydroxypropylacrylamide, 2-hydroxypropylmethacrylamide, 3-hydroxypropylacrylamide, 3-hydroxypropylmethacrylamide, 3-hydroxybutylacrylamide, 3-hydroxybutylmethacrylamide, 4-hydroxybutylacrylamide, 4-hydroxybutylmethacrylamide, 6-hydroxyhexylacrylamide, 6-hydroxyhexylmethacrylamide, 3-hydroxy-2-ethylhexylacrylamide and 3-hydroxy-2-ethylhexylmethacrylamide.

Suitable monomers b2.5) are polyether acrylates, which, for the purposes of this invention, are generally understood as meaning esters of α,β-ethylenically unsaturated mono- and dicarboxylic acids with polyetherols. Suitable polyetherols are linear or branched substances having terminal hydroxyl groups which comprise ether bonds. In general, they have a molecular weight in the range from about 150 to 20 000. Suitable polyetherols are polyalkylene glycols, such as polyethylene glycols, polypropylene glycols, polytetrahydrofurans and alkylene oxide copolymers. Suitable alkylene oxides for the preparation of alkylene oxide copolymers are, for example, ethylene oxide, propylene oxide, epichlorohydrin, 1,2- and 2,3-butylene oxide. The alkylene oxide copolymers can comprise the copolymerized alkylene oxide units in randomly distributed form or in the form of blocks. Preference is given to ethylene oxide/propylene oxide copolymers.

As component b2.5), preference is given to polyether acrylates of the general formula V

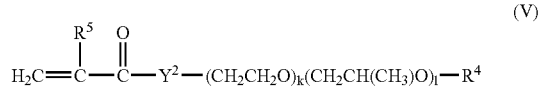

(V)

in which the order of the alkylene oxide units is arbitrary, k and l, independently of one another, are an integer from 0 to 1000, where the sum of k and l is at least 5, $R^4$ is hydrogen, $C_1$-$C_{30}$-alkyl or $C_5$-$C_8$-cycloalkyl, $R^5$ is hydrogen or $C_1$-$C_8$-alkyl, $Y^2$ is O or $NR^6$, where $R^6$ is hydrogen, $C_1$-$C_{30}$-alkyl or $C_5$-$C_8$-cycloalkyl.

Preferably, k is an integer from 1 to 500, in particular 3 to 250. Preferably, ll is an integer from 0 to 100.

Preferably, $R^5$ is hydrogen, methyl, ethyl, n-propyl, isopropyl, n-butyl, sec-butyl, tert-butyl, n-pentyl or n-hexyl, in particular hydrogen, methyl or ethyl.

Preferably, $R^4$ in the formula IV is hydrogen, methyl, ethyl, n-propyl, isopropyl, n-butyl, sec-butyl, n-pentyl, n-hexyl, octyl, 2-ethylhexyl, decyl, lauryl, palmityl or stearyl.

Preferably, $Y^2$ in the formula IV is O or NH.

Suitable polyether acrylates b2.5) are, for example, the polycondensation products of the abovementioned α,β-ethylenically unsaturated mono- and/or dicarboxylic acids and their acid chlorides, acid amides and anhydrides with polyetherols. Suitable polyetherols can be prepared easily by reacting ethylene oxide, 1,2-propylene oxide and/or epichlorohydrin with a starter molecule, such as water or a short-chain alcohol $R^4$—OH. The alkylene oxides can be used individually, alternately one after the other or as a mixture. The polyether acrylates c) can be used on their own or in mixtures to prepare the polymers used according to the invention.

Suitable polyether acrylates b2.5) are also urethane (meth) acrylates with alkylene oxide groups. Such compounds are described in DE 198 38 851 (component e2)), to which reference is hereby made in its entirety.

The abovementioned monomers b2) can be used individually or in the form of arbitrary mixtures.

In a preferred embodiment of the invention, the preparations comprise, as component A, a terpolymer which comprises 5 to 15% by weight of monomer a), 30 to 70% by weight of monomer b1) and 20 to 35% by weight of monomer b2) in copolymerized form, with the proviso that the sum of the amounts of the monomers a) to b2) is 100% by weight.

Monomer b3)

The copolymers A) can additionally comprise at least one water-soluble monomer b3) different from a), b1) and b2) in copolymerized form, which is chosen from α,β-ethylenically unsaturated water-soluble compounds with cationic hydrophilic groups.

Preferably, the content of monomer b3) is 0 to 30% by weight, particularly preferably 0 to 20% by weight, in particular 0 to 10% by weight, based on the total weight of the monomers used for the polymerization.

The cationic groups of component b3) are preferably nitrogen-containing groups, such as quaternary ammonium groups.

These charged cationic groups can be produced from the amine nitrogens by quaternization, e.g. using the alkylating agents specified above for component a). Examples of alkylating agents are $C_1$-$C_4$-alkyl halides or sulfates, such as ethyl chloride, ethyl bromide, methyl chloride, methyl bromide, dimethyl sulfate and diethyl sulfate. A quaternization can generally take place either before or else after the polymerization.

Suitable monomers b3) are the compounds obtainable by quaternizing component a). Examples of such charged monomers b3) are quaternized N-vinylimidazoles, in particular 3-methyl-1-vinylimidazolium chloride and methosulfate.

Suitable compounds b3) are also the quaternization products of the esters of α,β-ethylenically unsaturated mono- and dicarboxylic acids with aminoalcohols. Preferred aminoalcohols are $C_2$-$C_{12}$-aminoalcohols which are $C_1$-$C_8$-dialkylated on the amine nitrogen. Suitable as acid component of these esters are, for example, acrylic acid, methacrylic acid, fumaric acid, maleic acid, itaconic acid, crotonic acid, maleic anhydride, monobutyl maleate and mixtures thereof. Preference is given to using acrylic acid, methacrylic acid and mixtures thereof as acid component.

Preferred monomers b3) are the quaternization products of N,N-dimethylaminomethyl(meth)acrylate, N,N-dimethylaminoethyl(meth)acrylate, N,N-diethylaminoethyl(meth)acrylate, N,N-dimethylaminopropyl(meth)acrylate, N,N-diethylaminopropyl(meth)acrylate and N,N-dimethylaminocyclohexyl(meth)acrylate.

Suitable monomers b3) are also the quaternization products of the amides of the abovementioned α,β-ethylenically unsaturated mono- and dicarboxylic acids with diamines which have at least one primary or secondary amino group. Preference is given to diamines which have one tertiary and one primary or secondary amino group.

Suitable monomers b3) are, for example, the quaternization products of N-[2-(dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)butyl]methacrylamide, N-[2-(diethylamino)ethyl]acrylamide, N-[4-(dimethylamino)cyclohexyl]acrylamide and N-[4-(dimethylamino)cyclohexyl]methacrylamide.

Suitable monomers b3) are also the quaternization products of the N,N-diallylamines and N,N-diallyl-N-alkylamines. Alkyl here is preferably $C_1$-$C_{24}$-alkyl. Preference is given to N,N-diallyl-N,N-dimethylammonium compounds, such as, for example, the chlorides and bromides. These include, in particular, N,N-diallyl-N,N-dimethylammonium chloride (DADMAC).

Suitable monomers b3) are also the quaternization products of various vinyl- and allyl-substituted nitrogen heterocycles, such as 2- and 4-vinylpyridine, 2- and 4-allylpyridine.

The abovementioned monomers b3) can in each case be used individually or in the form of arbitrary mixtures.

In a preferred embodiment of the invention, the preparations comprise, as component A, a polymer which comprises 5 to 15% by weight of monomer a), 30 to 70% by weight of monomer b1), 20 to 35% by weight of monomer b2) and 0 to 10% by weight of monomer b3) in copolymerized form, with the proviso that the sum of the amounts of monomers a) to b3) is 100% by weight.

Monomer c)

The copolymers A) can additionally comprise at least one monomer c) different from the monomers a) to b3) in copolymerized form. The additional monomers c) are preferably chosen from esters of α,β-ethylenically unsaturated mono- and dicarboxylic acids with $C_1$-$C_{30}$-alkanols, N-alkyl- and N,N-dialkylamides, α,β-ethylenically unsaturated monocarboxylic acids which, in addition to the carbonyl carbon atom of the amide group, have at least 9 further carbon atoms, esters of vinyl alcohol and allyl alcohol with $C_1$-$C_{30}$-monocarboxylic acids, vinyl ethers, vinyl aromatics, vinyl halides, vinylidene halides, $C_1$-$C_8$-monoolefins, nonaromatic hydrocarbons with at least two conjugated double bonds and mixtures thereof.

Preferably, the content of monomers c) is 0 to 15% by weight, particularly preferably 0.1 to 10% by weight, based on the total weight of the monomers used for the polymerization.

Suitable additional monomers c) are methyl(meth)acrylate, methyl ethacrylate, ethyl(meth)acrylate, ethyl ethacrylate, n-butyl(meth)acrylate, tert-butyl(meth)acrylate, tert-butyl ethacrylate, n-octyl(meth)acrylate, 1,1,3,3-tetramethylbutyl(meth)acrylate, ethylhexyl(meth)acrylate, n-nonyl(meth)acrylate, n-decyl(meth)acrylate, n-undecyl(meth)acrylate, tridecyl(meth)acrylate, myristyl(meth)acrylate, pentadecyl(meth)acrylate, palmityl(meth)acrylate, heptadecyl(meth)acrylate, nonadecyl(meth)acrylate, arrachinyl(meth)acrylate, behenyl(meth)acrylate, lignocerenyl(meth)acrylate, cerotinyl(meth)acrylate, melissinyl(meth)acrylate, palmitoleinyl(meth)acrylate, oleyl(meth)acrylate, linolyl(meth)acrylate, linolenyl(meth)acrylate, stearyl(meth)acrylate, lauryl(meth)acrylate and mixtures thereof. Preferred monomers c) are the esters of α,β-ethylenically unsaturated mono- and dicarboxylic acids with $C_1$-$C_4$-alkanols.

Suitable additional monomers c) are also N-(n-octyl)(meth)acrylamide, N-(1,1,3,3-tetramethylbutyl)(meth)acrylamide, N-ethylhexyl(meth)acrylamide, N-(n-nonyl)(meth)acrylamide, N-(n-decyl)(meth)acrylamide, N-(n-undecyl)(meth)acrylamide, N-tridecyl(meth)acrylamide, N-myristyl(meth)acrylamide, N-pentadecyl(meth)acrylamide, N-palmityl(meth)acrylamide, N-heptadecyl(meth)acrylamide, N-nonadecyl(meth)acrylamide, N-arrachinyl(meth)acrylamide, N-behenyl(meth)acrylamide, N-lignocerenyl(meth)acrylamide, N-cerotinyl(meth)acrylamide, N-melissinyl(meth)acrylamide, N-palmitoleinyl(meth)acrylamide, N-oleyl(meth)acrylamide, N-linolyl(meth)acrylamide, N-linolenyl(meth)acrylamide, N-stearyl(meth)acrylamide, N-lauryl(meth)acrylamide.

Suitable additional monomers c) are also vinyl acetate, vinyl propionate, vinyl butyrate and mixtures thereof.

Suitable additional monomers c) are also ethylene, propylene, isobutylene, butadiene, styrene, α-methylstyrene, acrylonitrile, methacrylonitrile, vinyl chloride, vinylidene chloride, vinyl fluoride, vinylidene fluoride and mixtures thereof.

The abovementioned additional monomers c) can be used individually or in the form of arbitrary mixtures.

Crosslinker d)

The copolymers A) can, if desired, comprise at least one crosslinker, i.e. a compound with two or more than two ethylenically unsaturated, nonconjugated double bonds, in copolymerized form.

Crosslinkers are preferably used in an amount of from 0.01 to 3% by weight, particularly preferably 0.1 to 2% by weight, based on the total weight of the monomers used for the polymerization.

Suitable crosslinkers d) are, for example, acrylic esters, methacrylic esters, allyl ethers or vinyl ethers of at least dihydric alcohols. The OH groups of the parent alcohols may be completely or partially etherified or esterified; however, the crosslinkers comprise at least two ethylenically unsaturated groups.

Examples of the parent alcohols are dihydric alcohols, such as 1,2-ethanediol, 1,2-propanediol, 1,3-propanediol, 1,2-butanediol, 1,3-butanediol, 2,3-butanediol, 1,4-butanediol, but-2-en-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis(hydroxymethyl)cyclohexane, neopentyl glycol monohydroxypivalate, 2,2-bis(4-hydroxyphenyl)propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiopentane-1,5-diol, and polyethylene glycols, polypropylene glycols and polytetrahydrofurans with molecular weights of in each case 200 to 10 000. Apart from the homopolymers of ethylene oxide or propylene oxide, it is also possible to use block copolymers of ethylene oxide or propylene oxide or copolymers which comprise incorporated ethylene oxide and propylene oxide groups. Examples of parent alcohols with more than two OH groups are trimethylolpropane, glycerol, pentaerythritol, 1,2,5-pentanetriol, 1,2,6-hexanetriol, triethoxycyanuric acid, sorbitan, sugars, such as sucrose, glucose, mannose. The polyhydric alcohols can of course also be used following reaction with ethylene oxide or propylene oxide as the corresponding ethoxylates or propoxylates, respectively. The polyhydric alcohols can also firstly be converted to the corresponding glycidyl ethers by reaction with epichlorohydrin.

Further suitable crosslinkers d) are the vinyl esters or the esters of monohydric, unsaturated alcohols with ethylenically unsaturated $C_3$-$C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. It is, however, also possible to esterify the monohydric unsaturated alcohols with polybasic carboxylic acids, for example malonic acid, tartaric acid, trimellitic acid, phthalic acid, terephthalic acid, citric acid or succinic acid.

Further suitable crosslinkers d) are esters of unsaturated carboxylic acids with the above-described polyhydric alcohols, for example oleic acid, crotonic acid, cinnamic acid or 10-undecenoic acid.

Suitable crosslinkers d) are also straight-chain or branched, linear or cyclic, aliphatic or aromatic hydrocarbons which have at least two double bonds which, in the case of aliphatic hydrocarbons, must not be conjugated, e.g. divinylbenzene, divinyltoluene, 1,7-octadiene, 1,9-decadiene, 4-vinyl-1-cyclohexene, trivinylcyclohexane or polybutadienes with molecular weights of from 200 to 20 000.

Further suitable crosslinkers d) are the acrylamides, methacrylamides and N-allylamines of at least difunctional amines. Such amines are, for example, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Likewise suitable are the amides of allylamine and unsaturated carboxylic acids, such as acrylic acid, methacrylic acid, itaconic acid, maleic acid, or at least dibasic carboxylic acids, as have been described above.

Also suitable are triallylamine and triallylmonoalkylammonium salts, e.g. triallylmethylammonium chloride or methyl sulfate, as crosslinker d).

Also suitable are N-vinyl compounds of urea derivatives, at least difunctional amides, cyanurates or urethanes, for example of urea, ethyleneurea, propyleneurea or tartardiamide, e.g. N,N'-divinylethyleneurea or N,N'-divinylpropyleneurea.

Further suitable crosslinkers d) are divinyldioxane, tetraallylsilane or tetravinylsilane.

Mixtures of the abovementioned compounds d) can of course also be used. Preference is given to using water-soluble crosslinkers d).

Particularly preferably used crosslinkers d) are, for example, methylenebisacrylamide, triallylamine and triallylalkylammonium salts, divinylimidazole, pentaerythritol triallyl ether, N,N'-divinylethyleneurea, reaction products of polyhydric alcohols with acrylic acid or methacrylic acid, methacrylic esters and acrylic esters of polyalkylene oxides and polyhydric alcohols which have been reacted with ethylene oxide and/or propylene oxide and/or epichlorohydrin.

Very particularly preferred crosslinkers d) are pentaerythritol triallyl ether, methylenebisacrylamide, N,N'-divinylethyleneurea, triallylamine and triallylmonoalkylammonium salts and acrylic esters of glycol, butanediol, trimethylolpropane or glycerol or acrylic esters of glycol, butanediol, trimethylolpropane or glycerol reacted with ethylene oxide and/or epichlorohydrin.

Preference is given to preparations where the copolymer A) comprises
  a) N-vinylimidazole and/or a derivative thereof and
  b1) at least one N-vinyllactam
  b2) if appropriate at least one nonionic water-soluble monomer chosen from
    b2.1) N-vinylamides of saturated $C_1$-$C_8$-monocarboxylic acids,
    b2.2) primary amides of $\alpha,\beta$-ethylenically unsaturated monocarboxylic acids and their N-alkyl and N,N-dialkyl derivatives which, in addition to the carbonyl carbon atom of the amide group, have at most 8 further carbon atoms,
  b3) if appropriate at least one monomer chosen from the quaternization products of N-vinylimidazole and dimethylaminopropylmethacrylamide
in copolymerized form, where the pH of the aqueous preparation has a value in the range from pH 4 to pH 6.

Preference is also given to preparations where the copolymer A) comprises
  a) 0.5 to 40% by weight of N-vinylimidazole and/or a derivative thereof,
  b1) 20 to 99.5% by weight of at least one N-vinyllactam,
  b2) 0 to 50% by weight of at least one nonionic water-soluble monomer different from components a) and b1) and copolymerizable therewith, and
  b3) 0 to 30% by weight of at least one monomer which is chosen from $\alpha,\beta$-ethylenically unsaturated water-soluble compounds with cationic hydrophilic groups, with the proviso that the sum of the amounts of components a) to b3) is 100% by weight,
in copolymerized form, where the pH of the aqueous preparation has a value in the range from pH 4 to pH 6.

Preference is also given to preparations where the copolymer A) comprises
  a) 1 to 30% by weight of N-vinylimidazole and/or a derivative thereof,
  b1) 20 to 70% by weight of at least one N-vinyllactam,
  b2) 5 to 50% by weight of at least one nonionic water-soluble monomer different from components a) and b1) and copolymerizable therewith, and
  b3) 0 to 20% by weight of at least one monomer which is chosen from $\alpha,\beta$-ethylenically unsaturated water-soluble compounds with cationic hydrophilic groups, with the proviso that the sum of the amounts of components a) to b3) is 100% by weight,
in copolymerized form, where the pH of the aqueous preparation has a value in the range from pH 4 to pH 6.

Further preferred are preparations where the copolymer A) comprises
  a) 3 to 20% by weight of N-vinylimidazole and/or a derivative thereof,
  b1) 30 to 70% by weight of at least one N-vinyllactam,
  b2) 10 to 40% by weight of at least one nonionic water-soluble monomer different from the components a) and b1) and copolymerizable therewith, and
  b3) 0 to 10% by weight of at least one monomer which is chosen from $\alpha,\beta$-ethylenically unsaturated water-soluble compounds with cationic hydrophilic groups, with the proviso that the sum of the amounts of components a) to b3) is 100% by weight,
in copolymerized form, where the pH of the aqueous preparation has a value in the range from pH 4 to pH 6.

In a preferred embodiment, the copolymer A) consists only of repeat units which are derived from the abovementioned monomers a), b1) and if appropriate b2) and/or b3).

In a particularly preferred preparation, copolymer A) comprises
  a) 3 to 15% by weight of N-vinylimidazole
  b) 30 to 70% by weight of N-vinylpyrrolidone
  c) 20 to 35% by weight of methacrylamide
  d) 0 to 10% by weight of quaternized N-vinylimidazole
  with the proviso that the sum of the amounts of components a) to b3) is 100% by weight, in copolymerized form.

The copolymers A) are prepared in accordance with customary processes known to the person skilled in the art, e.g. by solution, precipitation, suspension or emulsion polymerization. Preference is given to preparation by solution or precipitation polymerization.

Preferred solvents for the solution polymerization are aqueous solvents, such as water and mixtures of water with water-miscible solvents, for example alcohols, such as methanol, ethanol, n-propanol, isopropanol, n-butanol, sec-butanol, tert-butanol, n-hexanol and cyclohexanol, and glycols, such as ethylene glycol, propylene glycol and butylene glycol, and the methyl or ethyl ethers of dihydric alcohols, diethylene glycol, triethylene glycol, polyethylene glycols with number-average molecular weights up to about 3000, glycerol and dioxane. Particular preference is given to the polymerization in water or a water/alcohol mixture, for example in a water/ethanol mixture.

If water is used as a solvent constituent, preferably demineralized water is used.

The precipitation polymerization takes place, for example, in an ester, such as ethyl acetate or butyl acetate, as solvent. The resulting polymer particles precipitate out of the reaction solution and can be isolated by customary methods, such as filtration by means of subatmospheric pressure. In precipitation polymerization, polymers with higher molecular weights are generally obtained than in solution polymerization.

The polymerization temperatures are preferably in a range from about 30 to 120° C., particularly preferably 40 to 100° C. The polymerization usually takes place under atmospheric pressure, although it can also proceed under reduced or increased pressure. A suitable pressure range is between 1 and 5 bar.

To prepare the polymers A), the monomers can be polymerized with the help of initiators which form free radicals.

Initiators which can be used for the free-radical polymerization are the peroxo and/or azo compounds customary for this purpose, for example alkali metal or ammonium peroxydisulfates, diacetyl peroxide, dibenzoyl peroxide, succinyl peroxide, di-tert-butyl peroxide, tert-butyl perbenzoate, tert-butyl perpivalate, tert-butyl peroxy-2-ethylhexanoate, tert-butyl permaleate, cumene hydroperoxide, diisopropyl peroxydicarbamate, bis(o-toluyl)peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azobisisobutyronitrile, 2,2'-azobis(2-amidinopropane)hydrochloride (V50 from Wako Pure Chemicals Industries, Ltd.), or 2,2'-azobis(2-methylbutyronitrile). Also suitable are initiator mixtures or redox initiator systems, such as, for example, ascorbic acid/iron(II) sulfate/sodium peroxodisulfate, tert-butyl hydroperoxide/sodium disulfite, tert-butyl hydroperoxide/sodium hydroxymethanesulfinate, $H_2O_2$/$Cu^r$.

To adjust the molecular weight, the polymerization can take place in the presence of at least one regulator. Regulators which may be used are the customary compounds known to the person skilled in the art, such as, for example, sulfur compounds, e.g. mercaptoethanol, 2-ethylhexyl thioglycolate, thioglycolic acid or dodecylmercaptan, and tribromochloromethane or other compounds which have a regulating effect on the molecular weight of the resulting polymers. A preferred regulator is cysteine.

To achieve the purest possible polymers with a low residual monomer content, the polymerization (main polymerization) may be followed by an afterpolymerization step. The afterpolymerization can take place in the presence of the same initiator system as or a different initiator system from the main polymerization. The afterpolymerization preferably takes place at least at the same temperature as, preferably at a higher temperature than, the main polymerization. If desired, the reaction mixture may, after the polymerization or between the first and the second polymerization step, be subjected to stripping with steam or to steam distillation.

According to the invention, the adjustment of the pH of the aqueous preparation to a value in the range from pH 4 to pH 6 can be carried out before or after stripping with steam or steam distillation.

If an organic solvent is used in the preparation of the polymers, then this can be removed by customary processes known to the person skilled in the art, e.g. by distillation at reduced pressure.

The polymerization preferably takes place at a pH in the range from 6 to 9, particularly preferably from 6.5 to 7.5. The pH is adjusted by adding a suitable acid or by adding a suitable base.

The resulting liquid polymer compositions can be converted to powder form by various drying processes, such as, for example, spray-drying, fluidized spray-drying, roll drying or freeze-drying. Preference is given to using spray-drying. The polymer dry powders obtained in this way can advantageously be converted again to an aqueous solution or dispersion by dissolution or redispersion, respectively, in water. Pulverulent copolymers have the advantage of better storability, easier transportability and generally have a lower propensity for microbial attack.

It is a further subject-matter of the invention to adjust the liquid polymer compositions to a pH in the range from pH 4 to pH 6 after polymerization is complete and before drying and/or converting to the powder form.

Cosmetically acceptable carrier B)

The preparations according to the invention have a cosmetically and/or pharmaceutically acceptable carrier B) which is chosen from
  i) water,
  ii) water-miscible organic solvents, preferably $C_2$-$C_4$-alkanols, in particular ethanol,
  iii) oils, fats, waxes,
  iv) esters of $C_6$-$C_{30}$-monocarboxylic acids with mono-, di- or trihydric alcohols which are different from iii),
  v) saturated acyclic and cyclic hydrocarbons,
  vi) fatty acids,
  vii) fatty alcohols,
  viii) propellant gases
  and mixtures thereof.

The preparations according to the invention have, for example, an oil or fat component B) which is chosen from: hydrocarbons of low polarity, such as mineral oils; linear saturated hydrocarbons, preferably with more than 8 carbon atoms, such as tetradecane, hexadecane, octadecane etc.; cyclic hydrocarbons, such as decahydronaphthalene; branched hydrocarbons; animal and vegetable oils; waxes; wax esters; petroleum jelly; esters, preferably esters of fatty acids, such as, for example, the esters of $C_1$-$C_{24}$-monoalcohols with $C_1$-$C_{22}$-monocarboxylic acids, such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate, tetratriacontanyl stearate; salicylates, such as $C_1$-$C_{10}$-salicylates, e.g. octyl salicylate; benzoate esters, such as $C_{10}$-$C_{15}$-alkyl benzoates, benzyl benzoate; other cosmetic esters, such as fatty acid triglycerides, propylene glycol monolaurate, polyethylene glycol monolaurate, $C_{10}$-$C_{15}$-alkyl lactates, etc. and mixtures thereof.

Suitable silicone oils B) are, for example, linear polydimethylsiloxanes, poly(methylphenylsiloxanes), cyclic siloxanes and mixtures thereof. The number-average molecular weight of the polydimethylsiloxanes and poly(methylphenylsiloxanes) is preferably in a range from about 1 000 to 150 000 g/mol. Preferred cyclic siloxanes have 4- to 8-membered rings. Suitable cyclic siloxanes are commercially available, for example, under the name cyclomethicone.

Preferred oil or fat components B) are chosen from paraffin and paraffin oils; petroleum jelly; natural fats and oils, such as castor oil, soybean oil, groundnut oil, olive oil, sunflower oil, sesame oil, avocado oil, cocoa butter, almond oil, peach kernel oil, castor oil, cod-liver oil, lard, spermaceti, spermaceti oil, sperm oil, wheatgerm oil, macadamia nut oil, evening primrose oil, jojoba oil; fatty alcohols, such as lauryl alcohol, myristyl alcohol, cetyl alcohol, stearyl alcohol, oleyl alcohol; fatty acids, such as myristic acid, stearic acid, palmitic acid, oleic acid, linoleic acid, linolenic acid and saturated, unsaturated and substituted fatty acids different therefrom; waxes, such as beeswax, carnauba wax, candililla wax, spermaceti and mixtures of the abovementioned oil and fat components.

Suitable cosmetically and pharmaceutically compatible oil or fat components B) are described in Karl-Heinz Schrader, Grundlagen und Rezepturen der Kosmetika [Fundamentals and formulations of cosmetics], 2nd edition, Verlag Hüthig, Heidelberg, pp. 319-355, which is hereby incorporated by reference.

Suitable hydrophilic carriers B) are chosen from water, 1-, 2- or polyhydric alcohols with preferably 1 to 8 carbon atoms, such as ethanol, n-propanol, isopropanol, propylene glycol, glycerol, sorbitol, etc.

The cosmetic preparations according to the invention may be skin cosmetic, hair cosmetic, dermatological, hygienic or pharmaceutical compositions. On the basis of their film-forming properties, the above-described preparations are suitable in particular for hair and skin cosmetics.

The preparations according to the invention are preferably in the form of a gel, foam, spray, mousse, ointment, cream, emulsion, suspension, lotion, milk or paste. If desired, liposomes or microspheres can also be used.

The cosmetically or pharmaceutically active preparations according to the invention can additionally comprise cosmetically and/or dermatologically active ingredients and auxiliaries.

The cosmetic preparations according to the invention preferably comprise at least one copolymer A) as defined above, at least one carrier B) as defined above and at least one constituent different therefrom which is chosen from cosmetically active ingredients, emulsifiers, surfactants, preservatives, perfume oils, thickeners, hair polymers, hair and skin conditioners, graft polymers, water-soluble or dispersible silicone-containing polymers, light protection agents, bleaches, gel formers, care agents, colorants, tinting agents, tanning agents, dyes, pigments, consistency-imparting agents, humectants, refatting agents, collagen, protein hydrolyzates, lipids, antioxidants, antifoams, antistats, emollients and softeners.

Customary thickeners in such formulations are crosslinked polyacrylic acids and derivatives thereof, polysaccharides and derivatives thereof, such as xanthan gum, agar agar, alginates or tyloses, cellulose derivatives, e.g. carboxymethylcellulose or hydroxycarboxymethylcellulose, fatty alcohols, monoglycerides and fatty acids, polyvinyl alcohol and polyvinylpyrrolidone. Preference is given to using nonionic thickeners.

Preferably, the preparations according to the invention additionally comprise at least one nonionic thickener.

Suitable cosmetically and/or dermatologially active ingredients are, for example, coloring active ingredients, skin and hair pigmentation agents, tinting agents, tanning agents, bleaches, keratin-hardening substances, antimicrobial active ingredients, light filter active ingredients, repellent active ingredients, substances with a hyperemic effect, substances with a keratolytic and keratoplastic effect, antidandruff active ingredients, antiphlogistics, substances with a keratinizing effect, active ingredients with an antioxidative effect or a free-radical scavenging effect, substances which wet the skin or retain moisture in the skin, refatting active ingredients, antierythematous or antiallergic active ingredients and mixtures thereof.

Active ingredients which tan the skin artificially and which are suitable for tanning the skin without natural or artificial irradiation with UV rays are, for example, dihydroxyacetone, alloxan and walnut shell extract. Suitable keratin-hardening substances are usually active ingredients as are also used in antiperspirants, such as, for example, potassium aluminum sulfate, aluminum hydroxychloride, aluminum lactate, etc. Antimicrobial active ingredients are used in order to destroy microorganisms or to inhibit their growth and thus serve both as preservatives and also as a deodorizing substance which reduces the formation or the intensity of body odor. These include, for example, customary preservatives known to the person skilled in the art, such as p-hydroxybenzoic esters, imidazolidinylurea, formaldehyde, sorbic acid, benzoic acid, salicylic acid, etc. Such deodorizing substances are, for example, zinc ricinoleate, triclosan, undecylenic acid alkylolamides, triethyl citrate, chlorhexidine etc. Suitable light filter active ingredients are substances which absorb UV rays in the UV-B and/or UV-A region. Suitable UV filters are, for example, 2,4,6-triaryl-1,3,5-triazines in which the aryl groups may in each case carry at least one substituent which is preferably chosen from hydroxy, alkoxy, specifically methoxy, alkoxycarbonyl, specifically methoxycarbonyl and ethoxycarbonyl and mixtures thereof. Also suitable are p-aminobenzoates, cinnamates, benzophenones, camphor derivatives, and pigments which stop UV rays, such as titanium dioxide, talc and zinc oxide. Suitable repellent active ingredients are compounds which are able to drive or keep certain animals, in particular insects, away from humans. These include, for example, 2-ethyl-1,3-hexanediol, N,N-diethyl-m-toluamide etc. Suitable substances with hyperemic activity, which stimulate blood flow through the skin are, for example, essential oils, such as dwarf pine, lavender, rosemary, juniperberry, roast chestnut extract, birch leaf extract, hayseed extract, ethyl acetate, camphor, menthol, peppermint oil, rosemary extract, eucalyptus oil, etc. Suitable keratolytic and keratoplastic substances are, for example, salicylic acid, calcium thioglycolate, thioglycolic acid and its salts, sulfur, etc. Suitable antidandruff active ingredients are, for example, sulfur, sulfur polyethylene glycol sorbitan monooleate, sulfur ricinol polyethoxylate, zinc pyrithione, aluminum pyrithione, etc. Suitable antiphlogistics, which counter skin irritations, are, for example, allantoin, bisabolol, Dragosantol, camomile extract, panthenol, etc.

The cosmetic preparations according to the invention can comprise, as cosmetic and/or pharmaceutical active ingredient (and also, if appropriate, as auxiliary), at least one further cosmetically or pharmaceutically acceptable polymer. These include, quite generally, cationic, amphoteric and neutral polymers.

The aqueous preparations according to the invention can also comprise water-soluble polymers different from copolymer A).

Suitable polymers are, for example, cationic polymers with the INCI name Polyquaternium, e.g. copolymers of vinylpyrrolidone/N-vinylimidazolium salts (Luviquat® FC, Luviquat® HM, Luviquat® MS, Luviquat® Care, Luviquat® UltraCare), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (Polyquaternium-4 and -10), acrylamido copolymers (Polyquaternium-7) and chitosan. Suitable cationic (quaternized) polymers are also Merquat® (polymer based on dimethyldiallylammonium chloride), Gafquat® (quaternary polymers which are formed by the reaction of polyvinylpyrrolidone with quaternary ammonium compounds), Polymer JR (hydroxyethylcellulose with cationic groups) and plant-based cationic polymers, e.g. guar polymers, such as the Jaguar® grades from Rhodia.

Further suitable polymers are also neutral polymers, such as polyvinylpyrrolidones, copolymers of N-vinylpyrrolidone and vinyl acetate and/or vinyl propionate and/or stearyl (meth)acrylate, polysiloxanes, polyvinylcaprolactam and other copolymers with N-vinylpyrrolidone, polyethylenimines and salts thereof, polyvinylamines and salts thereof, cellulose derivatives, polyaspartic acid salts and derivatives.

These include, for example, Luviflex® Swing (partially hydrolyzed copolymer of polyvinyl acetate and polyethylene glycol, BASF) or Kollicoat® IR.

Suitable polymers are also those described in WO 03/092640, in particular the (meth)acrylamide copolymers described as Examples 1 to 50 (Table 1, page 40 ff.) and Examples 51 to 65 (Table 2, page 43), to which reference is made at this point in its entirety.

Suitable polymers are also nonionic, water-soluble or water-dispersible polymers or oligomers, such as polyvinylcaprolactam, e.g. Luviskol® Plus (BASF) or polyvinylpyrrolidone and copolymers thereof, in particular with vinyl esters, such as vinyl acetate, e.g. Luviskol® VA 37 (BASF); polyamides, e.g. based on itaconic acid and aliphatic diamines, as are described, for example, in DE-A-43 33 238.

Suitable polymers are also amphoteric or zwitterionic polymers, such as the octyl acrylamide/methyl methacrylate/tert-butylaminoethyl methacrylate/2-hydroxypropyl methacrylate copolymers which are available under the name Amphomer® (National Starch) and zwitterionic polymers as are disclosed, for example, in German patent applications DE 39 29 973, DE 21 50 557, DE 28 17 369 and DE 37 08 451. Acrylamidopropyltrimethylammonium chloride/acrylic acid or methacrylic acid copolymers and alkali metal and ammonium salts thereof are preferred zwitterionic polymers. Further suitable zwitterionic polymers are methacroylethylbetaine/methacrylate copolymers which are available commercially under the name Amersette® (AMERCHOL), and copolymers of hydroxyethyl methacrylate, methyl methacrylate, N,N-dimethylaminoethyl methacrylate and acrylic acid (Jordapon®).

Suitable polymers are also nonionic, siloxane-containing, water-soluble or -dispersible polymers, e.g. polyethersiloxanes, such as Tegopren® (Goldschmidt) or Belsil® (Wacker).

Also suitable are further biopolymers, i.e. polymers which are obtained from naturally renewable raw materials and are made up of natural monomer building blocks, e.g. cellulose derivatives, chitin, chitosan, DNA, hyaluronic acid and RNA derivatives.

Further preparations according to the invention comprise at least one further water-soluble polymer, in particular chitosans (poly(D-glucosamines)) of varying molecular weight and/or chitosan derivatives.

Anionic Polymers

Further polymers suitable for the preparations according to the invention are copolymers containing carboxylic acid groups. These are polyelectrolytes with a relatively large number of anionically dissociatable groups in the main chain and/or a side chain. They are able to form polyelectrolyte complexes with the copolymers A) (symplexes).

In a preferred embodiment, the polyelectrolyte complexes used in the compositions according to the invention have an excess of anionogenic/anionic groups.

As well as comprising at least one of the abovementioned copolymers A), the polyelectrolyte complexes also comprise at least one acid-group-containing polymer.

The polyelectrolyte complexes preferably comprise copolymer(s) A) and acid-group-containing polymers in a quantitative weight ratio of from 50:1 to 1:20, particularly preferably from 20:1 to 1:5.

Suitable carboxylic acid-group-containing polymers are obtainable, for example, by free-radical polymerization of α,β-ethylenically unsaturated monomers. Monomers m1) are used here which comprise at least one free-radically polymerizable, α,β-ethylenically unsaturated double bond and at least one anionogenic and/or anionic group per molecule.

Suitable carboxylic-acid-group-containing polymers are also carboxylic-acid-group-containing polyurethanes.

The monomers are preferably chosen from monoethylenically unsaturated carboxylic acids, sulfonic acids, phosphonic acids and mixtures thereof.

The monomers m1) include monoethylenically unsaturated mono- and dicarboxylic acids having 3 to 25, preferably 3 to 6, carbon atoms, which may also be used in the form of their salts or anhydrides. Examples thereof are acrylic acid, methacrylic acid, ethacrylic acid, α-chloroacrylic acid, crotonic acid, maleic acid, maleic anhydride, itaconic acid, citraconic acid, mesaconic acid, glutaconic acid, aconitic acid and fumaric acid. The monomers also include the half-esters of monoethylenically unsaturated dicarboxylic acids having 4 to 10, preferably 4 to 6, carbon atoms, e.g. of maleic acid, such as monomethyl maleate. The monomers also include monoethylenically unsaturated sulfonic acids and phosphonic acids, for example vinylsulfonic acid, allylsulfonic acid, sulfoethyl acrylate, sulfoethyl methacrylate, sulfopropyl acrylate, sulfopropyl methacrylate, 2-hydroxy-3-acryloxypropylsulfonic acid, 2-hydroxy-3-methacryloxypropylsulfonic acid, styrenesulfonic acid, 2-acrylamido-2-methylpropanesulfonic acid, vinylphosphonic acid and allylphosophonic acid. The monomers also include the salts of the abovementioned acids, in particular the sodium, potassium and ammonium salts, and the salts with the abovementioned amines. The monomers can be used as such or as mixtures with one another. The weight fractions given all refer to the acid form.

The monomer m1) is preferably chosen from acrylic acid, methacrylic acid, ethacrylic acid, α-chloroacrylic acid, crotonic acid, maleic acid, maleic anhydride, fumaric acid, itaconic acid, citraconic acid, mesaconic acid, glutaconic acid, aconitic acid and mixtures thereof, particularly preferably acrylic acid, methacrylic acid and mixtures therof.

The abovementioned monomers m1) can in each case be used individually or in the form of arbitrary mixtures.

Comonomers which are suitable in principle for the preparation of the carboxylic-acid-group-containing polymers are the compounds a) to d) specified above as components of the copolymer A), with the proviso that the molar fraction of anionogenic and anionic groups which the carboxylic-acid-group-containing polymer comprises in copolymerized form is greater than the molar fraction of cationogenic and cationic groups.

In a preferred embodiment, the carboxylic-acid-group-containing polymers comprise at least one monomer in copolymerized form which is chosen from the abovementioned crosslinkers d). Reference is made to suitable and preferred crosslinkers d).

The carboxylic-acid-group-containing polymers further preferably comprise at least one monomer m2) in copolymerized form, which is chosen from compounds of the general formula (VI)

in which
R$^1$ is hydrogen or C$_1$-C$_8$-alkyl,
Y$^1$ is O, NH or NR$^3$, and
R$^2$ and R$^3$, independently of one another, are C$_1$-C$_{30}$-alkyl or C$_5$-C$_8$-cycloalkyl, where the alkyl groups may be interrupted by up to four nonadjacent heteroatoms or heteroatom-containing groups chosen from O, S and NH.

Preferably, $R^1$ in the formula VI is hydrogen or $C_1$-$C_4$-alkyl, in particular hydrogen, methyl or ethyl.

Preferably, $R^2$ in the formula VI is $C_1$-$C_8$-alkyl, preferably methyl, ethyl, n-butyl, isobutyl, tert-butyl or a group of the formula —$CH_2$—$CH_2$—NH—$C(CH_3)_3$.

If $R^3$ is alkyl, then it is preferably $C_1$-$C_4$-alkyl, such as methyl, ethyl, n-propyl, n-butyl, isobutyl or tert-butyl.

Suitable monomers m2) are methyl(meth)acrylate, methyl ethacrylate, ethyl(meth)acrylate, ethyl ethacrylate, tert-butyl (meth)acrylate, tert-butyl ethacrylate, n-octyl(meth)acrylate, 1,1,3,3-tetramethylbutyl(meth)acrylate, ethylhexyl(meth) acrylate, n-nonyl(meth)acrylate, n-decyl(meth)acrylate, n-undecyl(meth)acrylate, tridecyl(meth)acrylate, myristyl (meth)acrylate, pentadecyl(meth)acrylate, palmityl(meth) acrylate, heptadecyl(meth)acrylate, nonadecyl(meth)acrylate, arrachinyl(meth)acrylate, behenyl(meth)acrylate, lignocerenyl(meth)acrylate, cerotinyl(meth)acrylate, melissinyl(meth)acrylate, palmitoleinyl(meth)acrylate, oleyl (meth)acrylate, linolyl(meth)acrylate, linolenyl(meth)acrylate, stearyl(meth)acrylate, lauryl(meth)acrylate and mixtures thereof.

Suitable monomers m2) are also acrylamide, methacrylmide, N-methyl(meth)acrylamide, N-ethyl(meth)acrylamide, N-propyl(meth)acrylamide, N-(n-butyl)(meth)acrylamide, N-(tert-butyl)(meth)acrylamide, N,N-dimethyl (meth)acrylamide, N,N-diethyl(meth)acrylamide piperidinyl (meth)acrylamide and morpholinyl(meth)acrylamide, N-(n-octyl)(meth)acrylamide, N-(1,1,3,3-tetramethylbutyl)(meth) acrylamide, N-ethylhexyl(meth)acrylamide, N-(n-nonyl) (meth)acrylamide, N-(n-decyl)(meth)acrylamide, N-(n-undecyl)(meth)acrylamide, N-tridecyl(meth)acrylamide, N-myristyl(meth)acrylamide, N-pentadecyl(meth)acrylamide, N-palmityl(meth)acrylamide, N-heptadecyl(meth) acrylamide, N-nonadecyl(meth)acrylamide, N-arrachinyl (meth)acrylamide, N-behenyl(meth)acrylamide, N-lignocerenyl(meth)acrylamide, N-cerotinyl(meth)acrylamide, N-melissinyl(meth)acrylamide, N-palmitoleinyl (meth)acrylamide, N-oleyl(meth)acrylamide, N-linolyl (meth)acrylamide, N-linolenyl(meth)acrylamide, N-stearyl (meth)acrylamide and N-lauryl(meth)acrylamide.

Furthermore, the carboxylic-acid-group-containing polymers preferably comprise at least one monomer m3) in copolymerized form which is chosen from compounds of the general formula VII

(VII)

in which
the order of the alkylene oxide units is arbitrary,
k and l, independently of one another, are an integer from 0 to 1000, where the sum of k and l is at least 5,
$R^4$ is hydrogen, $C_1$-$C_{30}$-alkyl or $C_5$-$C_8$-cycloalkyl,
$R^5$ is hydrogen or $C_1$-$C_8$-alkyl,
$Y^2$ is O or $NR^6$, where $R^6$ is hydrogen, $C_1$-$C_{30}$-alkyl or $C_5$-$C_8$-cycloalkyl.

Preferably, in the formula VII, k is an integer from 1 to 500, in particular 3 to 250. l is preferably an integer from 0 to 100.

Preferably, $R^5$ is hydrogen, methyl, ethyl, n-propyl, isopropyl, n-butyl, sec-butyl, tert-butyl, n-pentyl or n-hexyl, in particular hydrogen, methyl or ethyl.

Preferably, $R^4$ in the formula VII is hydrogen, methyl, ethyl, n-propyl, isopropyl, n-butyl, sec-butyl, n-pentyl, n-hexyl, octyl, 2-ethylhexyl, decyl, lauryl, palmityl or stearyl.

Preferably, $Y^2$ in the formula VII is O or NH.

Suitable polyether acrylates VII) are, for example, the polycondensation products of the abovementioned α,β-ethylenically unsaturated mono- and/or dicarboxylic acids and the acid chlorides, amides and anhydrides thereof with polyetherols. Suitable polyetherols can be prepared easily by reacting ethylene oxide, 1,2-propylene oxide and/or epi-chlorohydrin with a starter molecule, such as water or a short-chain alcohol $R^4$—OH. The alkylene oxides can be used individually, alternately one after the other or as a mixture. The polyether acrylates VII) can be used on their own or in mixtures for the preparation of the polymers used according to the invention. Suitable polyether acrylates II) are also urethane (meth)acrylates with alkylene oxide groups. Such compounds are described in DE 198 38 851 (component e2)), which is hereby incorporated in its entirety by reference.

Anionic polymers preferred as carboxylic-acid-group-containing polymers are, for example, homopolymers and copolymers of acrylic acid and methacrylic acid and salts thereof. These also include crosslinked polymers of acrylic acid, as are available under the INCI name Carbomer. Such crosslinked homopolymers of acrylic acid are available commercially, for example under the name Carbopol® from Noveon. Preference is also given to hydrophobically modified crosslinked polyacrylate polymers, such as Carbopol® Ultrez 21 from Noveon.

Polyelectrolyte complexes based on homopolymers and copolymers of acrylic acid and methacrylic acid are suitable in an advantageous manner for formulation as gels, for example for setting gels, and also for the formulation of foams.

Further examples of suitable anionic polymers are copolymers of acrylic acid and acrylamide and salts thereof; sodium salts of polyhydroxycarboxylic acids, water-soluble or water-dispersible polyesters, polyurethanes and polyureas. Particularly suitable polymers are copolymers of (meth)acrylic acid and polyether acrylates, where the polyether chain is terminated with a $C_8$-$C_{30}$-alkyl radical. These include, for example, acrylate/beheneth-25 methacrylate copolymers which are available under the name Aculyn® from Rohm und Haas. Particularly suitable polymers are also copolymers of t-butyl acrylate, ethyl acrylate, methacrylic acid (e.g. Luvimer® 100P, Luvimer® Pro55), copolymers of ethyl acrylate and methacrylic acid (e.g. Luvimer® MAE), copolymers of N-tert-butylacrylamide, ethyl acrylate, acrylic acid (Ultrahold® 8, Ultrahold® Strong), copolymers of vinyl acetate, crotonic acid and if appropriate further vinyl esters (e.g. Luviset® grades), maleic anhydride copolymers, if appropriate reacted with alcohol, anionic polysiloxanes, e.g. carboxy-functional, t-butyl acrylate, methacrylic acid (e.g. Luviskol® VBM), copolymers of acrylic acid and methacrylic acid with hydrophobic monomers, such as, for example, $C_4$-$C_{30}$-alkyl esters of meth(acrylic acid), $C_4$-$C_{30}$-alkyl vinyl esters, $C_4$-$C_{30}$-alkyl vinyl ethers and hyaluronic acid. Examples of anionic polymers are also vinyl acetate/crotonic acid copolymers, as are available commercially, for example, under the names Resyn® (National Starch) and Gafset® (GAF) and vinylpyrrolidone/vinyl acrylate copolymers obtainable, for example, under the trade name Luviflex® (BASF). Further suitable polymers are the vinylpyrrolidone/acrylate terpolymer available under the name Luviflex® VBM-36 (BASF) and sodium sulfonate-containing polyamides or sodium sulfonate-containing polyesters.

The group of suitable anionic polymers also includes, for example, Balance® CR (National Starch; acrylate copolymer), Balance® 0/55 (National Starch; acrylates copolymer), Balance® 47 (National Starch; octylacrylamide/acrylates/butylaminoethyl methacrylate copolymer), Aquaflex® FX 64 (ISP; isobutylene/ethylmaleimide/hydroxy-ethylmaleimide copolymer), Aquaflex® SF-40 (ISP/National Starch; VP/vinylcaprolactam/DMAPA acrylate copolymer), Allianz® LT-120 (ISP/Rohm & Haas; acrylate/C1-2 succinate/hydroxyacrylate copolymer), Aquarez® HS (Eastman; polyester-1), Diaformer® Z-400 (Clariant; methacryloylethylbetaine/methacrylate copolymer), Diaformer® Z-711 (Clariant; methacryloylethyl N-oxide/methacrylate copolymer), Diaformer® Z-712 (Clariant; methacryloylethyl N-oxide/methacrylate copolymer), Omnirez® 2000 (ISP; monoethyl ester of poly(methyl vinyl ether/maleic acid in ethanol), Amphomer® HC (National Starch; acrylate/octylacrylamide copolymer), Amphomer® 28-4910 (National Starch; octylacrylamide/acrylate/butyl-aminoethyl methacrylate copolymer), Advantage® HC 37 (ISP; terpolymer of vinylcaprolactam/vinylpyrrolidone/dimethylaminoethyl methacrylate), Advantage® LC55 and LC80 or LC A and LC E, Advantage® Plus (ISP; VA/butyl maleate/isobornyl acrylate copolymer), Aculyne® 258 (Rohm & Haas; acrylate/hydroxy ester acrylate copolymer), Luviset® P.U.R. (BASF, polyurethane-1), Luviflex® Silk (BASF), Eastman® AQ 48 (Eastman), Styleze® CC-10 (ISP; VP/DMAPA acrylates copolymer), Styleze® 2000 (ISP; VP/acrylates/lauryl methacrylate copolymer), DynamX® (National Starch; polyurethane-14 AMP-acrylates copolymer), Resyn XP® (National Starch; acrylates/octylacrylamide copolymer), Fixomer® A-30 (Ondeo Nalco; polymethacrylic acid (and) acrylamidomethylpropanesulfonic acid), Fixate® G-100 (Noveon; AMP-acrylates/allyl methacrylate copolymer).

Suitable carboxylic-acid-group-containing polymers are also the terpolymers of vinylpyrrolidone/$C_1$-$C_{10}$-alkyl, cycloalkyl and aryl(meth)acrylates and acrylic acid described in U.S. Pat. No. 3,405,084. Suitable carboxylic-acid-group-containing polymers are also the terpolymers of vinylpyrrolidone, tert-butyl(meth)acrylate and (meth)acrylic acid described in EP-A-0 257 444 and EP-A-0 480 280. Suitable carboxylic-acid-group-containing polymers are also the copolymers described in DE-A42 23 066 which comprise at least one (meth)acrylic ester, (meth)acrylic acid, and N-vinylpyrrolidone and/or N-vinylcaprolactam in copolymerized form. Reference is hereby made to the disclosure of these documents.

The preparation of the abovementioned carboxylic acid-group-containing polymers is carried out by known processes, for example of solution, precipitation, suspension or emulsion polymerization, as described above for the copolymers A).

Suitable carboxylic-acid-group-containing polymers are also carboxylic-acid-group-containing polyurethanes.

EP-A-636361 discloses suitable block copolymers with polysiloxane blocks and polyurethane/polyurea blocks which have carboxylic acid and/or sulfonic acid groups. Suitable silicone-containing polyurethanes are also described in WO 97/25021 and EP-A-751 162.

Suitable polyurethanes are also described in DE-A42 25 045, which is hereby incorporated in its entirety by reference.

The acid groups of the carboxylic-acid-group-containing polymers can be partially or completely neutralized. At least some of the acid groups are then in deprotonated form, the counterions preferably being chosen from alkali metal ions, such as $Na^+$, $K^+$, ammonium ions and organic derivatives thereof etc.

The preparations according to the invention can also be used in the field of pharmacy. The formulation base of pharmaceutical preparations according to the invention preferably comprises pharmaceutically acceptable auxiliaries. Pharmaceutically acceptable auxiliaries are the auxiliaries which are known for use in the field of pharmacy, food technology and related fields, in particular those listed in the relevant pharmacopoeia (e.g. DAB Ph. Eur. BP NF), and other auxiliaries whose properties do not preclude a physiological application.

Suitable auxiliaries may be: lubricants, wetting agents, emulsifying and suspending agents, preservatives, antioxidants, antiirritative substances, chelating agents, emulsion stabilizers, film formers, gel formers, odor-masking agents, resins, hydrocolloids, solvents, solubility promoters, neutralizing agents, permeation accelerators, pigments, quaternary ammonium compounds, refatting and superfatting agents, ointment bases, cream bases or oil bases, silicone derivatives, stabilizers, sterilizing agents, propellants, drying agents, opacifiers, thickeners, waxes, softeners, white oils. Formulation in this regard is based on specialist knowledge, as given, for example, in Fiedler, H. P. Lexikon der Hilfsstoffe für Pharmazie, Kosmetik und angrenzende Gebiete [Lexicon of auxiliaries for pharmacy, cosmetics and related fields], 4th ed., Aulendorf: ECV-Editio-Kantor-Verlag, 1996.

To prepare the dermatological preparations according to the invention, the active ingredients can be mixed or diluted with a suitable auxiliary (excipient). Excipients may be solid, semisolid or liquid materials which can serve as vehicles, carriers or medium for the active ingredient. The admixing of further auxiliaries is carried out, where desired, in the manner known to the person-skilled in the art. In addition, the preparations are suitable as auxiliaries in pharmacy, preferably in coating(s) or binder(s) for solid drug forms. They can also be used in creams and as tablet coatings and tablet binders.

According to a preferred embodiment, the preparations according to the invention are a skin-cleansing composition.

Preferred skin-cleansing preparations are soaps of liquid to gel-like consistency, such as transparent soaps, luxury soaps, deodorant soaps, cream soaps, baby soaps, skin protection soaps, abrasive soaps and syndets, pasty soaps, soft soaps and washing pastes, liquid washing, shower and bath preparations, such as washing lotions, shower baths and shower gels, foam baths, oil baths and scrub preparations, shaving foams, lotions and creams.

According to a further preferred embodiment, the preparations according to the invention are cosmetic preparations for the care and protection of the skin, nailcare compositions or preparations for decorative cosmetics.

Suitable skin cosmetic preparations are, for example, face tonics, face masks, deodorants and other cosmetic lotions. Compositions for use in decorative cosmetics include, for example, concealer pencils, stage makeup, mascara and eyeshadows, lipsticks, kohl pencils, eyeliners, blushers, powders and eyebrow pencils.

The skincare compositions according to the invention are, in particular, W/O or O/W skin creams, day and night creams, eye creams, face creams, antiwrinkle creams, moisturizing creams, bleaching creams, vitamin creams, skin lotions, care lotions and moisturizing lotions.

Skin cosmetic and dermatological compositions based on the above-described preparations exhibit advantageous effects. The preparations can, inter alia, contribute to the moisturization and conditioning of the skin and to an improvement in the feel of the skin. The preparations can also act as thickeners in the formulations. By adding the polymers according to the invention, it is possible to achieve a considerable improvement in skin compatibility in certain formulations.

Skin cosmetic and dermatological preparations according to the invention preferably comprise at least one copolymer A) in an amount of from about 0.001 to 30% by weight, preferably 0.01 to 20% by weight, very particularly preferably 0.1 to 12% by weight, based on the total weight of the composition.

Light protection agents based on the copolymers A) in particular have the property of increasing the residence time of the UV-absorbing ingredients compared with customary auxiliaries such as polyvinylpyrrolidone.

Depending on the field of use, the compositions according to the invention can be applied in a form suitable for skincare, such as, for example, in the form of a cream, foam, gel, pencil, mousse, milk, spray (pump spray or spray containing propellant) or lotion.

As well as comprising the copolymers A) and suitable carriers, the skin cosmetic preparations according to the invention can also comprise further active ingredients and auxiliaries customary in skin cosmetics and as described above. These include, preferably, emulsifiers, preservatives, perfume oils, cosmetic active ingredients, such as phytantriol, vitamin A, E and C, retinol, bisabolol, panthenol, light protection agents, bleaches, colorants, tinting agents, tanning agents, collagen, protein hydrolyzates, stabilizers, pH regulators, dyes, salts, thickeners, gel formers, consistency-imparting agents, silicones, humectants, refatting agents and further customary additives.

Preferred oil and fat components of the skin cosmetic and dermatological compositions are the abovementioned mineral and synthetic oils, such as, for example, paraffins, silicone oils and aliphatic hydrocarbons with more than 8 carbon atoms, animal and vegetable oils, such as, for example, sunflower oil, coconut oil, avocado oil, olive oil, lanolin, or waxes, fatty acids, fatty acid esters, such as, for example, triglycerides of $C_6$-$C_{30}$-fatty acids, wax esters, such as, for example, jojoba oil, fatty alcohols, petroleum jelly, hydrogenated lanolin and acetylated lanolin, and mixtures thereof.

The preparations according to the invention can also comprise conventional polymers where specific properties are to be set.

To set certain properties, such as, for example, improving the feel to the touch, the spreading behavior, the water resistance and/or the binding of active ingredients and auxiliaries, such as pigments, the skin cosmetic and dermatological preparations can additionally also comprise conditioning substances based on silicone compounds. Suitable silicone compounds are, for example, polyalkylsiloxanes, polyarylsiloxanes, polyarylalkylsiloxanes, polyether siloxanes or silicone resins.

The cosmetic or dermatological preparations are prepared by customary processes known to the person skilled in the art.

The cosmetic and dermatological compositions are preferably in the form of emulsions, in particular in the form of water-in-oil (W/O) or oil-in-water (O/W) emulsions. It is, however, also possible to choose other types of formulation, for example hydrodispersions, gels, oils, oleogels, multiple emulsions, for example in the form of W/O/W or O/W/O emulsions, anhydrous ointments or ointment bases, etc.

The emulsions are prepared by known methods. Apart from at least one copolymer A), the emulsions usually comprise customary constituents, such as fatty alcohols, fatty acid esters and in particular fatty acid triglycerides, fatty acids, lanolin and derivatives thereof, natural or synthetic oils or waxes and emulsifiers in the presence of water. The choice of emulsion type-specific additives and the preparation of suitable emulsions is described, for example, in Schrader, Grundlagen und Rezepturen der Kosmetika [Fundamentals and formulations of cosmetics], Hüthig Buch Verlag, Heidelberg, 2nd edition, 1989, third part, which is hereby expressly incorporated by reference.

A suitable emulsion, e.g. for a skin cream etc., generally comprises an aqueous phase which is emulsified by means of a suitable emulsifier system in an oil or fatty phase. A preparation according to the invention can be used to prepare the aqueous phase.

Preferred fatty components which may be present in the fatty phase of the emulsions are: hydrocarbon oils, such as paraffin oil, purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karité oil, hoplostethus oil; mineral oils whose distillation start-point under atmospheric pressure is about 250° C. and whose distillation end-point is 410° C., such as, for example, vaseline oil; esters of saturated or unsaturated fatty acids, such as alkyl myristates, e.g. i-propyl, butyl or cetyl myristate, hexadecyl stearate, ethyl or isopropyl palmitate, octanoic or decanoic acid triglycerides and cetyl ricinoleate.

The fatty phase can also comprise silicone oils soluble in other oils, such as dimethylpolysiloxane, methylphenylpolysiloxane and the silicone glycol copolymer, fatty acids and fatty alcohols.

Besides the copolymers A), it is also possible to use waxes, such as, for example, carnauba wax, candililla wax, beeswax, microcrystalline wax, ozocerite wax and Ca, Mg and Al oleate, myristates, linoleates and stearates.

In addition, an emulsion according to the invention may be present in the form of an O/W emulsion. An emulsion of this type usually comprises an oil phase, emulsifiers which stabilize the oil phase in the water phase, and an aqueous phase which is usually present in thickened form. Suitable emulsifiers are preferably O/W emulsifiers, such as polyglycerol esters, sorbitan esters and partially esterified glycerides.

According to a further preferred embodiment, the preparations according to the invention are a shower gel, a shampoo formulation or a bath preparation.

Such formulations according to the invention comprise at least one copolymer A) and also usually anionic surfactants as base surfactants and amphoteric and/or nonionic surfactants as cosurfactants. Further suitable active ingredients and/or auxiliaries are generally chosen from lipids, perfume oils, dyes, organic acids, preservatives and antioxidants, and also thickeners/gel formers, skin conditioning agents and humectants.

These formulations preferably comprise 2 to 50% by weight, preferably 5 to 40% by weight, particularly preferably 8 to 30% by weight, of surfactants, based on the total weight of the formulation.

All anionic, neutral, amphoteric or cationic surfactants customarily used in body-cleansing compositions can be used in the washing, shower and bath preparations.

Suitable anionic surfactants are, for example, alkyl sulfates, alkyl ether sulfates, alkylsulfonates, alkylarylsulfonates, alkyl succinates, alkyl sulfosuccinates, N-alkoylsarcosinates, acyl taurates, acyl isothionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

These include, for example, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkylbetaines, alkylamidopropylbetaines; alkylsulfobetaines, alkyl glycinates, alkyl carboxyglycinates, alkyl amphoacetates or alkyl amphopropionates, alkyl amphodiacetates or alkyl amphodipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mol per mole of alcohol. Also suitable are alkylamine oxides, mono- or dialkylalkanolamides, fatty acid esters of polyethylene glycols, ethoxylated fatty acid amides, alkyl polyglycosides or sorbitan ether esters.

The washing, shower and bath preparations can also comprise customary cationic surfactants, such as, for example, quaternary ammonium compounds, for example cetyltrimethylammonium chloride.

In addition, the shower gel/shampoo formulations may comprise thickeners, such as, for example, sodium chloride, PEG-55, propylene glycol oleate, PEG-120-methylglucose dioleate and others, and also preservatives, further active ingredients and auxiliaries and water.

According to a further preferred embodiment, the preparations according to the invention are a hair-treatment composition.

Hair-treatment compositions according to the invention preferably comprise at least one copolymer A) in an amount in the range from about 0.1 to 30% by weight, preferably 0.5 to 20% by weight, based on the total weight of the composition.

The hair-treatment compositions according to the invention are preferably in the form of a setting foam, hair mousse, hair gel, shampoo, hairspray, hair foam, end fluid, neutralizing agent for permanent waves, hair colorant and bleach or hot-oil treatment. Depending on the field of use, the hair cosmetic preparations can be applied in the form of an (aerosol) spray, (aerosol) foam, gel, gel spray, cream, lotion or wax. Hairsprays include both aerosol sprays and also pump sprays without propellant gas. Hair foams include both aerosol foams and also pump foams without propellant gas. Hairsprays and hair foams preferably comprise predominantly or exclusively water-soluble or water-dispersible components. If the compounds used in the hairsprays and hair foams according to the invention are water-dispersible, they can be applied in the form of aqueous microdispersions with particle diameters of usually 1 to 350 nm, preferably 1 to 250 nm. The solids contents of these preparations here are usually in a range from about 0.5 to 20% by weight. These microdispersions generally require no emulsifiers or surfactants for their stabilization.

In a preferred embodiment, the hair cosmetic formulations according to the invention comprise
A) 0.05 to 20% by weight of at least one copolymer A)
B) 20 to 99.95% by weight of water and/or alcohol,
C) 0 to 50% by weight of at least one propellant gas,
D) 0 to 5% by weight of at least one emulsifier,
E) 0 to 3% by weight of at least one thickener, and
F) up to 25% by weight of further constituents
where the pH of the formulation has a value in the range from pH 4 to pH 6.

Alcohol is understood as meaning all alcohols customary in cosmetics, e.g. ethanol, isopropanol, n-propanol.

Further constituents are understood as meaning the additives customary in cosmetics, for example propellants, antifoams, interface-active compounds, i.e. surfactants, emulsifiers, foam formers and solubilizers. The interface-active compounds used may be anionic, cationic, amphoteric or neutral. Further customary constituents may also be, for example, preservatives, perfume oils, opacifiers, active ingredients, UV filters, care substances, such as panthenol, collagen, vitamins, protein hydrolyzates, alpha- and beta-hydroxycarboxylic acids, stabilizers, pH regulators, dyes, viscosity regulators, gel formers, salts, humectants, refatting agents, complexing agents and further customary additives.

These also include all styling and conditioning polymers known in cosmetics which may be used in combination with the polymers according to the invention if very particular properties are to be set.

Suitable conventional hair cosmetic polymers are, for example, the abovementioned cationic, anionic, neutral, nonionic and amphoteric polymers, which are hereby incorporated by reference.

To set certain properties, the preparations can additionally also comprise conditioning substances based on silicone compounds. Suitable silicone compounds are, for example, polyalkylsiloxanes, polyarylsiloxanes, polyarylalkylsiloxanes, polyether siloxanes, silicone resins or dimethicone copolyols (CTFA) and aminofunctional silicone compounds such as amodimethicone (CTFA).

The polymers according to the invention are suitable in particular as setting agents in hairstyling preparations, in particular hairsprays (aerosol sprays and pump sprays without propellant gas) and hair foams (aerosol foams and pump foams without propellant gas).

In a preferred embodiment, spray preparations comprise
A) 0.1 to 3% by weight of at least one copolymer A),
B) 0.1 to 3% by weight of at least one further polymer,
C) 20 to 99.9% by weight of water and/or alcohol,
D) 0 to 70% by weight of at least one propellant,
E) 0 to 20% by weight of further constituents,
where the pH of the preparation has a value in the range from pH 4 to pH 6.

Propellants are the propellants customarily used for hair sprays or aerosol foams. Preference is given to mixtures of propane/butane, pentane, dimethyl ether, 1,1-difluoroethane (HFC-152 a), carbon dioxide, nitrogen or compressed air.

A formulation for aerosol hair foams preferred according to the invention comprises
A) 0.1 to 10% by weight of at least one copolymer A),
B) 55 to 99.8% by weight of water and/or alcohol,
C) 5 to 20% by weight of a propellant,
D) 0.1 to 5% by weight of an emulsifier,
E) 0 to 10% by weight of further constituents,
where the pH of the preparation has a value in the range from pH 4 to pH 6.

Emulsifiers which may be used are all emulsifiers customarily used in hair foams. Suitable emulsifiers may be nonionic, cationic or anionic or amphoteric.

Examples of nonionic emulsifiers (INCI nomenclature) are Laureths, e.g. Laureth-4; Ceteths, e.g. Ceteth-1, polyethylene glycol cetyl ether; Ceteareths, e.g. Ceteareth-25, polyglycol fatty acid glycerides, hydroxylated lecithin, lactyl esters of fatty acids, alkyl polyglycosides.

Examples of cationic emulsifiers are cetyldimethyl-2-hydroxyethylammonium dihydrogenphosphate, cetyltrimonium chloride, cetyltrimonium bromide, cocotrimonium methylsulfate, Quaternium-1 to x (INCI).

Anionic emulsifiers can, for example, be chosen from the group of alkyl sulfates, alkyl ether sulfates, alkylsulfonates, alkylarylsulfonates, alkyl succinates, alkyl sulfosuccinates, N-alkoylsarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

A preparation suitable according to the invention for styling gels can, for example, have the following composition:
A) 0.1 to 10% by weight of at least one copolymer A),
B) 80 to 99.85% by weight of water and/or alcohol,
C) 0 to 3% by weight, preferably 0.05 to 2% by weight, of a gel former,
D) 0 to 20% by weight of further constituents,
where the pH of the preparation has a value in the range from pH 4 to pH 6.

The use of gel formers may be advantageous in order to establish specific rheological or other performance properties of the gels. Gel formers which can be used are all gel formers customary in cosmetics.

These include, for example, cellulose derivatives, e.g. hydroxypropylcellulose, hydroxyethylcellulose, cationically modified celluloses, polysaccharides, e.g. xanthan gum, caprylic/capric triglyceride, sodium acrylate copolymers, Polyquaternium-32 (and) Paraffinum Liquidum (INCI), sodium acrylate copolymers (and) Paraffinum Liquidum (and) PPG-1 Trideceth-6, Acrylamidopropyl Trimonium Chloride/Acrylamide Copolymers, Steareth-10 Allyl Ether Acrylate Copolymers, Polyquaternium-37 (and) Paraffinum Liquidum (and) PPG-1 Trideceth-6, Polyquaternium 37 (and) Propylene Glycol Dicaprate Dicaprylate (and) PPG-1 Trideceth-6, Polyquaternium-7, Polyquaternium-44.

The preparations according to the invention can be used in cosmetic preparations as conditioning agents.

The preparations according to the invention can preferably be used in shampoo formulations as setting and/or conditioning agents. Preferred shampoo formulations comprise
A) 0.05 to 10% by weight of at least one copolymer A),
B) 25 to 94.95% by weight of water,
C) 5 to 50% by weight of surfactants,
D) 0 to 5% by weight of a further conditioning agent,
E) 0 to 10% by weight of further cosmetic constituents,
where the pH of the preparation has a value in the range from pH 4 to pH 6.

All anionic, neutral, amphoteric or cationic surfactants customarily used in shampoos can be used in the shampoo formulations.

Suitable anionic surfactants are, for example, alkyl sulfates, alkyl ether sulfates, alkylsulfonates, alkylarylsulfonates, alkyl succinates, alkyl sulfosuccinates, N-alkoylsarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

For example, sodium lauryl sulfate, ammonium lauryl sulfate, sodium lauryl ether sulfate, ammonium lauryl ether sulfate, sodium lauroyl sarcosinate, sodium oleyl succinate, ammonium lauryl sulfosuccinate, sodium dodecylbenzenesulfonate, triethanolamine dodecylbenzenesulfonate are suitable.

Suitable amphoteric surfactants are, for example, alkylbetaines, alkylamidopropylbetaines, alkylsulfobetaines, alkyl glycinates, alkyl carboxyglycinates, alkyl amphoacetates or amphopropionates, alkyl amphodiacetates or amphodipropionates.

For example, cocodimethylsulfopropylbetaine, laurylbetaine, cocamidopropylbetaine or sodium cocamphopropionate can be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mol per mole of alcohol. Also suitable are alkylamine oxides, mono- or dialkylalkanolamides, fatty acid esters of polyethylene glycols, alkylpolyglycosides or sorbitan ether esters.

Furthermore, the shampoo formulations can comprise customary cationic surfactants, such as, for example, quaternary ammonium compounds, for example cetyltrimethylammonium chloride.

In the shampoo formulations, customary conditioning agents can be used in combination with the copolymers A) to achieve certain effects. These include, for example, the abovementioned cationic polymers with the INCI name Polyquaternium, in particular copolymers of vinylpyrrolidone/N-vinylimidazolium salts (Luviquat® FC, Luviquat® HM, Luviquat® MS, Luviquat® Care, Luviquat® Ultra-Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (Polyquaternium-4 and -10), acrylamide copolymers (Polyquaternium-7). It is also possible to use protein hydrolyzates, and conditioning substances based on silicone compounds, for example polyalkylsiloxanes, polyarylsiloxanes, polyarylalkylsiloxanes, polyether siloxanes or silicone resins. Further suitable silicone compounds are dimethicone copolyols (CTFA) and amino-functional silicone compounds, such as amodimethicones (CTFA). In addition, cationic guar derivatives, such as guar hydroxypropyltrimonium chloride (INCI), can be used.

The invention is illustrated in more detail by reference to the following nonlimiting examples.

EXAMPLES

The monomers are given in % by weight.

1. Preparation of Copolymers (Free-Radical Polymerization in Solution)

Example S1

Copolymer of N-vinylpyrrolidone (VP)/N-vinylimidazole (VI)/methacrylamide (MAM) (55/10/35)

| Initial charge: | Monomer mixture of |
|---|---|
| 121.5 g | demineralized (=demin.) water |
| 17.5 g | methacrylamide solution (15% strength by weight in water) |
| 0.75 g | N-vinylimidazole |
| 4.12 g | N-vinylpyrrolidone |
| 0.03 g | Wako ® V 50 [2,2'-azobis(2-amidinopropane) dihydrochloride] |

| Feed 1: | Monomer mixture of: |
|---|---|
| 78.5 g | N-vinylpyrrolidone |
| 14.2 g | N-vinylimidazole |
| 332 g | methacrylamide solution (15% strength by weight in water) |

| Feed 2: | Initiator solution of: |
|---|---|
| 0.6 g | Wako ® V 50 |
| 20.97 g | demin. water |

| Feed 3: | Initiator solution of: |
|---|---|
| 0.45 g | Wako ® V 50 |
| 10.5 g | demin. water |

In a 1 l pilot stirrer with metering, reflux condenser, internal thermometer and 3 separate feed devices, the initial charge was heated to 70° C. under a nitrogen atmosphere and with stirring. Upon reaching the temperature of 70° C., feed 1 was metered in over three hours and feed 2 was metered in over four hours. The mixture was then after-polymerized for two hours.

At 70° C., feed 3 was metered in over 10 minutes and the mixture was after-polymerized again for four hours. The mixture was then subjected to steam distillation for 30 minutes and cooled to 40° C.

Example S2

Copolymer of N-vinylpyrrolidone (VP)/N-vinylimidazole (VI)/methacrylamide (MAM)/N-vinylimidazole methosulfate (QVI) (60/5/30/5)

| Initial charge: | Monomer mixture of |
|---|---|
| 164 g | demin. water |
| 14.4 g | methacrylamide solution (15% strength by weight in water) |
| 0.36 g | N-vinylimidazole |
| 4.32 g | N-vinylpyrrolidone |
| 0.8 g | N-vinylimidazole methosulfate solution (45% strength by weight in water) |
| 0.04 g | Wako ® V 50 [2,2'-azobis(2-amidinopropane) dihydrochloride] |

| Feed 1: | Monomer mixture of: |
|---|---|
| 86.0 g | N-vinylpyrrolidone |
| 7.1 g | N-vinylimidazole |
| 285.0 g | methacrylamide solution (15% strength by weight in water) |
| 16.0 g | N-vinylimidazole methosulfate solution (45% strength by weight in water) |

| Feed 2: | Initiator solution of: |
|---|---|
| 0.85 g | Wako ® V 50 |
| 20.97 g | demin. water |

| Feed 3: | Initiator solution of: |
|---|---|
| 0.45 g | Wako ® V 50 |
| 10.49 g | demin. water |

In a 1 l pilot stirrer with metering, reflux condenser, internal thermometer and 3 separate feed devices, the initial charge was heated to 65° C. under a nitrogen atmosphere and with stirring. Upon reaching the temperature of 65° C., feed 1 was metered in over three hours and feed 2 was metered in over four hours. The mixture was then after-polymerized for two hours.

At 65° C., feed 3 was metered in over 10 minutes and the mixture was after-polymerized again for four hours. The mixture was then subjected to steam distillation for 30 minutes and cooled to 40° C.

Example S3

Copolymer of N-vinylpyrrolidone (VP)/N-vinylimidazole (VI)/methacrylamide (MAM)/N-vinylimidazole methosulfate (QVI) (55/5/35/5)

| Initial charge: | Monomer mixture of |
|---|---|
| 121.5 g | demin. water |
| 17.5 g | methacrylamide solution (15% strength by weight in water) |
| 0.37 g | N-vinylimidazole |
| 4.1 g | N-vinylpyrrolidone |
| 0.82 g | N-vinylimidazole methosulfate solution (45% strength by weight in water) |
| 0.04 g | Wako ® V 50 [2,2'-azobis(2-amidinopropane)dihydrochloride] |

| Feed 1: | Monomer mixture of: |
|---|---|
| 78 g | N-vinylpyrrolidone |
| 7.1 g | N-vinylimidazole |
| 332.5 g | methacrylamide solution (15% strength by weight in water) |
| 15.9 g | N-vinylimidazole methosulfate solution (45% strength by weight in water) |

| Feed 2: | Initiator solution of: |
|---|---|
| 0.70 g | Wako ® V 50 |
| 20.97 g | demin. water |

| Feed 3: | Initiator solution of: |
|---|---|
| 0.45 g | Wako ® V 50 |
| 10.49 g | demin. water |

In a 1 l pilot stirrer with metering, reflux condenser, internal thermometer and 3 separate feed devices, the initial charge was heated to 70° C. under a nitrogen atmosphere and with stirring. Feed 1 was adjusted to a pH of 5.5 by adding lactic acid. Upon reaching the temperature of 70° C., feed 1 was metered in over three hours and feed 2 was metered in over four hours. The mixture was then after-polymerized for two hours.

At 70° C., feed 3 was metered in over 10 minutes and the mixture was after-polymerized again for four hours. The mixture was then subjected to steam distillation for 30 minutes and cooled to 40° C.

Example S4

Copolymer of N-vinylpyrrolidone (VP)/N-vinylimidazole (VI)/methacrylamide (MAM)/N-vinylimidazole methosulfate (QVI) (55/5/35/5)

| Initial charge: | Monomer mixture of |
|---|---|
| 121.5 g | demin. water |
| 17.5 g | methacrylamide solution (15% strength by weight in water) |
| 0.37 g | N-vinylimidazole |
| 4.04 g | N-vinylpyrrolidone |
| 0.82 g | N-vinylimidazole methosulfate solution (45% strength by weight in water) |
| 0.04 g | Wako ® V 50 [2,2'-azobis(2-amidinopropane) dihydrochloride] |
| Feed 1: | Monomer mixture of: |
| 78 g | N-vinylpyrrolidone |
| 7.1 g | N-vinylimidazole |
| 332.5 g | methacrylamide solution (15% strength by weight in water) |
| 15.9 g | N-vinylimidazole methosulfate solution (45% strength by weight in water) |
| Feed 2: | Initiator solution of: |
| 0.70 g | Wako ® V 50 |
| 20.97 g | demin. water |
| Feed 3: | Initiator solution of: |
| 0.45 g | Wako ® V 50 |
| 10.49 g | demin. water |

In a 1 l pilot stirrer with metering, reflux condenser, internal thermometer and 3 separate feed devices, the initial charge was heated to 70° C. under a nitrogen atmosphere and with stirring. Upon reaching the temperature of 70° C., feed 1 was metered in over three hours and feed 2 was metered in over four hours. The mixture was then after-polymerized for two hours.

At 70° C., feed 3 was metered in over 10 minutes and the mixture was after-polymerized again for four hours. The mixture was then subjected to steam distillation for 30 minutes and cooled to 40° C.

Example S5

Copolymer of N-vinylpyrrolidone (VP)/N-vinylimidazole (VI)/methacrylamide (MAM) (55110135)

| Initial charge: | Monomer mixture of |
|---|---|
| 121.5 g | demin. water |
| 17.5 g | methacrylamide solution (15% strength by weight in water) |
| 0.75 g | N-vinylimidazole |
| 4.10 g | N-vinylpyrrolidone |
| 0.03 g | Wako ® V 50 [2,2'-azobis(2-amidinopropane) dihydrochloride] |
| Feed 1: | Monomer mixture of: |
| 78.0 g | N-vinylpyrrolidone |
| 14.0 g | N-vinylimidazole |
| 332.5 g | methacrylamide solution (15% strength by weight in water) |
| Feed 2: | Initiator solution of: |
| 0.55 g | Wako ® V 50 |
| 20.97 g | demin. water |
| Feed 3: | Initiator solution of: |
| 0.45 g | Wako ® V 50 |
| 10.49 g | demin. water |

In a 1 l pilot stirrer with metering, reflux condenser, internal thermometer and 3 separate feed devices, the initial charge was heated to 70° C. under a nitrogen atmosphere and with stirring. Feed 1 was adjusted to a pH of 5.5 by adding lactic acid. Upon reaching the temperature of 70° C., feed 1 was metered in over three hours and feed 2 was metered in over four hours. The mixture was then after-polymerized for two hours.

At 70° C., feed 3 was metered in over 10 minutes and the mixture was after-polymerized again for four hours. The mixture was then subjected to steam distillation for 30 minutes and cooled to 40° C.

Example S6

Copolymer of N-vinylpyrrolidone (VP)/N-vinylimidazole (VI)/methacrylamide (MAM) (55/10/35)

| Initial charge: | Monomer mixture of |
|---|---|
| 121 g | demin. water |
| 17.65 g | methacrylamide solution (15% strength by weight in water) |
| 0.7 g | N-vinylimidazole |
| 3.77 g | N-vinylpyrrolidone |
| 0.03 g | Wako ® V 50 [2,2'-azobis(2-amidinopropane) dihydrochloride] |
| 0.3 g | lactic acid |
| Feed 1: | Monomer mixture of: |
| 79.0 g | N-vinylpyrrolidone |
| 14.0 g | N-vinylimidazole |
| Feed 2: | Monomer mixture of: |
| 332.0 g | methacrylamide solution (15% strength by weight in water) |
| 4.8 g | lactic acid |
| Feed 3: | Initiator solution of: |
| 0.6 g | Wako ® V 50 |
| 20.97 g | demin. water |
| Feed 4: | Initiator solution of |
| 0.45 g | Wako ® V 50 |
| 10.5 g | demin. water |

In a 1 l pilot stirrer with metering, reflux condenser, internal thermometer and 4 separate feed devices, the initial charge was heated to 70° C. under a nitrogen atmosphere and with stirring. Upon reaching the temperature of 70° C., feed 1 was metered in over three hours and feeds 2 and 3 were metered in over four hours. The mixture was then after-polymerized for two hours. At 70° C., feed 3 was metered in over 10 minutes and the mixture was after-polymerized again for four hours. The mixture was then subjected to steam distillation for 30 minutes and cooled to 40° C.

Example S7

Copolymer of N-vinylpyrrolidone (VP)/N-vinylimidazole (VI)/methacrylamide (MAM)/N-vinylimidazole methosulfate (QVI) (551513515)

| Initial charge: | Monomer mixture of |
| --- | --- |
| 121.5 g | demin. water |
| 17.5 g | methacrylamide solution (15% strength by weight in water) |
| 0.37 g | N-vinylimidazole |
| 4.10 g | N-vinylpyrrolidone |
| 0.83 g | N-vinylimidazole methosulfate solution (45% strength by weight in water) |
| 0.04 g | Wako ® V 50 [2,2-azobis(2-amidinopropane) dihydrochloride] |
| Feed 2: | Monomer mixture of: |
| 79.0 g | N-vinylpyrrolidone |
| 16.0 | N-vinylimidazole methosulfate solution (45% strength by weight in water) |
| 7.1 g | N-vinylimidazole |
| Feed 1: | Monomer mixture of: |
| 332.0 g | methacrylamide solution (15% strength by weight in water) |
| Feed 3: | Initiator solution of: |
| 0.70 g | Wako ® V 50 |
| 20.97 g | demin. water |
| Feed 4: | Initiator solution of |
| 0.45 g | Wako ® V 50 |
| 10.49 g | demin. water |

In a 1 l pilot stirrer with metering, reflux condenser, internal thermometer and 4 separate feed devices, the initial charge was heated to 65° C. under a nitrogen atmosphere and with stirring. Feed 2 was adjusted to a value of 6.0 by adding lactic acid. Upon reaching the temperature of 65° C., feeds 1 and 3 were metered in over four hours and feed 2 was metered in over three hours. The mixture was then after-polymerized for two hours. At 65° C., feed 4 was metered in over 10 minutes and the mixture was after-polymerized again for four hours. The mixture was then subjected to steam distillation for 30 minutes and cooled to 40° C., the pH was adjusted to a value of pH 5.5 by adding lactic acid.

Example S8

Copolymer of N-vinylpyrrolidone (VP)/N-vinylimidazole (VI)/methacrylamide (MAM)/N-vinylimidazole methosulfate (QVI) (55/8/29/8)

| Initial charge: | Monomer mixture of |
| --- | --- |
| 166.0 g | demin. water |
| 15.7 g | methacrylamide solution (15% strength by weight in water) |
| 0.65 g | N-vinylimidazole |
| 4.45 g | N-vinylpyrrolidone |
| 1.45 g | N-vinylimidazole methosulfate solution (45% strength by weight in water) |
| 0.04 g | Wako ® V 50 [2,2'-azobis(2-amidinopropane) dihydrochloride] |
| Feed 1: | Monomer mixture of: |
| 274.0 g | methacrylamide solution (15% strength by weight in water) |
| 78 g | N-vinylpyrrolidone |
| 25.2 g | N-vinylimidazole methosulfate solution (45% strength by weight in water) |
| 11.3 g | N-vinylimidazole |
| Feed 2: | Initiator solution of: |
| 0.70 g | Wako ® V 50 |
| 20.97 g | demin. water |
| Feed 3: | Initiator solution of |
| 0.45 g | Wako ® V 50 |
| 10.49 g | demin. water |

In a 1 l pilot stirrer with metering, reflux condenser, internal thermometer and 3 separate feed devices, the initial charge was heated to 70° C. under a nitrogen atmosphere and with stirring. Feed 1 was adjusted to a pH of 6.0 by adding lactic acid. Upon reaching the temperature of 70° C., feed 1 was metered in over three hours and feed 2 was metered in over four hours. The mixture was then after-polymerized for two hours. At 70° C., feed 3 was metered in over 10 minutes and the mixture was after-polymerized again for four hours. The mixture was then subjected to steam distillation for 30 minutes and cooled to 40° C. The pH was adjusted to a value of pH 5.5 by adding lactic acid.

Example S9

Copolymer of N-vinylpyrrolidone (VP)/N-vinylimidazole (VI)/methacrylamide (MAM)/N-vinylimidazole methochloride (QVI) (55/10/29/6)

| Initial charge: | Monomer mixture of |
| --- | --- |
| 166.0 g | demin. water |
| 15.7 g | methacrylamide solution (15% strength by weight in water) |
| 0.80 g | N-vinylimidazole |
| 4.45 g | N-vinylpyrrolidone |
| 1.10 g | N-vinylimidazole methochloride solution (45% strength by weight in water) |

| | |
|---|---|
| 0.04 g | Wako ® V 50 [2,2'-azobis(2-amidinopropane) dihydrochloride] |
| Feed 1: | Monomer mixture of: |
| 274.0 g | methacrylamide solution (15% strength by weight in water) |
| 78.0 g | N-vinylpyrrolidone |
| 19.0 g | N-vinylimidazole methochloride solution (45% strength by weight in water) |
| 14.2 g | N-vinylimidazole |
| Feed 2: | Initiator solution of: |
| 0.70 g | Wako ® V 50 |
| 20.97 g | demin. water |
| Feed 3: | Initiator solution of |
| 0.45 g | Wako ® V 50 |
| 10.49 g | demin. water |

In a 1 l pilot stirrer with metering, reflux condenser, internal thermometer and 3 separate feed devices, the initial charge was heated to 70° C. under a nitrogen atmosphere and with stirring. Feed 1 was adjusted to a pH of 6.0 by adding lactic acid. Upon reaching the temperature of 70° C., feed 1 was metered in over three hours and feed 2 was metered in over four hours. The mixture was then after-polymerized for two hours. At 70° C., feed 3 was metered in over 10 minutes and the mixture was after-polymerized again for four hours. The mixture was then subjected to steam distillation for 30 minutes and cooled to 40° C.

Example S10

Copolymer of N-vinylpyrrolidone (VP)/N-vinylimidazole (VI)/methacrylamide (MAM)/N-vinylimidazole methosulfate (QVI) (55/10/2916)

| | |
|---|---|
| Initial charge: | Monomer mixture of |
| 324.0 g | demin. water |
| 31.8 g | methacrylamide solution (15% strength by weight in water) |
| 1.6 g | N-vinylimidazole |
| 9.0 g | N-vinylpyrrolidone |
| 2.2 g | N-vinylimidazole methosulfate solution (45% strength by weight in water) |
| 0.08 g | Wako ® V 50 [2,2'-azobis(2-amidinopropane) dihydrochloride] |
| Feed 1: | Monomer mixture of: |
| 548.0 g | methacrylamide solution (15% strength by weight in water) |
| 156 g | N-vinylpyrrolidone |
| 37.8 g | N-vinylimidazole methosulfate solution (45% strength by weight in water) |
| 28.5 g | N-vinylimidazole |
| Feed 2: | Initiator solution of: |
| 1.4 g | Wako ® V 50 |
| 41.9 g | demin. water |
| Feed 3: | Solution of |
| 1.28 g | 70% strength tert.-butyl hydroperoxide |
| 20 g | demin. water |
| Feed 4: | Solution of |
| 0.76 g | sodium disulfite |
| 11 g | demin. water |

In a 2 l pilot stirrer with metering, reflux condenser, internal thermometer and 3 separate feed devices, the initial charge was heated to 70° C. under a nitrogen atmosphere and with stirring. Feed 1 was adjusted to a pH of 6.5 by adding phosphoric acid. Upon reaching the temperature of 70° C., feed 1 was metered in over three hours and feed 2 was metered in over four hours. The mixture was then after-polymerized for two hours. The temperature was increased to 75° C. At 75° C., feed 3 was metered in batchwise. After 10 minutes feed 4 was added in 2 portions over 5 minutes and the mixture was after-polymerized for 3 hours. The mixture was then subjected to steam distillation for 30 minutes and cooled to 40° C.

Example S11

Copolymer of N-vinylpyrrolidone VP)/dimethylaminopropylmethacrylamide (DMAPMAM)/methacrylamide (MAM)

| | |
|---|---|
| Initial charge: | Monomer mixture of |
| 121.5 g | demin. water |
| 17.5 g | methacrylamide solution (15% strength by weight in water) |
| 0.75 g | dimethylaminopropylmethacrylamide |
| 4.12 g | N-vinylpyrrolidone |
| 0.03 g | Wako ® V 50 [2,2'-azobis(2-amidinopropane) dihydrochloride] |
| Feed 1: | Monomer mixture of: |
| 82.5 g | N-vinylpyrrolidone |
| 15 g | dimethylaminopropylmethacrylamide |
| 350 g | methacrylamide solution (15% strength by weight in water) |
| Feed 2: | Initiator solution of: |
| 0.6 g | Wako ® V 50 |
| 20.97 g | water |
| Feed 3: | Initiator solultion of: |
| 0.45 g | Wako ® V 50 |
| 10.5 g | water |

In a 1 l pilot stirrer with metering, reflux condenser, internal thermometer and 3 separate feed devices, the initial charge was heated to 70° C. under a nitrogen atmosphere and with stirring. Upon reaching the temperature of 70° C., feed 1 was metered in over three hours and feed 2 was metered in over four hours. The mixture was then after-polymerized for two hours.

At 70° C., feed 3 was metered in over 10 minutes and the mixture was after-polymerized again for four hours. The mixture was then subjected to steam distillation for 30 minutes and cooled to 40° C.

Application Examples

The copolymers synthesized according to Synthesis Examples S1 to S11 were prepared corresponding to the following composition as foam formulations (Examples SF1 to SF16).

SF1-SF16: Foam Formulations:

| | |
|---|---|
| 2.00 g | Luviquat ® Mono LS |
| 0.20 g | perfume oil |
| 2.00 g | AI* polymer |
| 0.10 g | Euxyl ® K 100 |
| q.s. | Phenonip ® |
| ad 100 g | water demin. |
| 10.00 g | propane/butane 3.5 bar |

*AI: Active ingredient polymer stands for the mass of polymer in g in 100 g of the overall formulation Preparation: The components were weighed in and homogenized slowly at room temperature with stirring. The preparation was then bottled in a suitable container and the propellant gas was added.

SF2, SF4, SF7, SF9, SF14: The pH of the foam formulations based on the polymers according to the details in Table 2 was adjusted to the pH given in Table 2 using lactic acid.

SF11 and SF12 are foam formulations in which the pH of the aqueous preparation has been adjusted after the polymerization is complete but before formulation in the form of a foam.

SF16, SF18: the pH of the foam formulation based on the polymer according to the details in Table 2 was adjusted to the pH given in Table 2 using phosphoric acid.

SF1, SF3, SF5, SF6, SF8, SF10, SF13 and SF15 are foam formulations in which the pH of the aqueous preparation has not been adjusted after polymerization is complete (comparative examples).

Determination of the K Value

The K values are measured in accordance with Fikentscher, Cellulosechemie [Cellulose Chemistry], Vol. 13, pp. 58 to 64 (1932) at 25° C. in aqueous/ethanolic or ethanolic solution and are a measure of the molar weight. The aqueous/ethanolic or ethanolic solution of the polymers comprises 1 g of polymer in 100 ml of solution. If the polymers are in the form of aqueous dispersions, corresponding amounts of the dispersion, depending on the polymer content of the dispersion, are topped up to 100 ml with ethanol such that the concentration is 1 g of polymer in 100 ml of solution. The K value is measured in a Micro-Ubbelohde capillary type M Ic from Schott.

Calculation of the K Value with Mixing Correction for Water in Ethanol

The factors listed below in the equation for the mixing correction refer exclusively to this type of capillary at a measurement temperature of 25° C.

Calculation of the K Value:

$$K = k*1000; z = \eta_{rel}$$

$$k = \frac{(1.5 \log z - 1)c \pm \sqrt{[(1.5 \log z - 1)^2 c^2 + 4(75c + 1.5c^2)(\log z)]}}{2(75c + 1.5c^2)}$$

Relative Viscosity:

$$\eta_{rel} = (t_{SLN} - HC_{SLN})/(t_{SOL} - HC_{SOL})$$

Calculation of the mixing correction:

Mixtures of water in ethanol exhibit nonproportional changes in the viscosity of the solvent mixture relative to the content of water.

Due to the nature of the sample (aqueous dispersion of a polymer), water is introduced into the ethanolic sample solution through the initial weight of the sample. This amount of water is included in the run time of the solvent by virtue of the mixing correction, such that the relative viscosity is corrected appropriately to the addition of water.

Run time of the solvent mixture:

$$t_{SOL} = t_o + t_M$$

Run time correction:

$$t_M = -7.486100e-5*c_W^4 + 3.785884 E-3*c_W^3 - 8.063441 E-2*c_W^2 + 1.999207*c_W + 2.959258E-2$$

Water content in solvent:

$$c_W = c/SC/100*(1-SC/100)$$

c concentration of the measurement solution [g/100 ml]
$c_W$ concentration of water in the measurement solution [g/100 ml]
SC solids content in the sample [g/100 g]
$HC_{SOL}$ Hagenbach correction of the solvent [-s]
$HC_{SLN}$ Hagenbach correction of the measurement solution [-s]
$t_{SOL}$ Run time of the solvent, mixing-corrected [s]
$t_{SLN}$ Run time of the measurement solution, measured [s]
$t_0$ Run time of the solvent, measured [s]
$t_M$ Run time correction for the solvent mixture, calculated [s]
z $\eta_{rel}$ in the Fikentscher equation (K value calculation)

Curl Retention:

The damp hair tress is pressed between filter paper, immersed three times into the polymer solution (formulation without propellant gas), in between stripped with the fingers and pressed again between filter papers. The hair is then wound around a Teflon rod and fixed using filter paper and rubber ring. The hair tresses are then dried in a heating cabinet at 70 to 80° C. for about 90 min. After cooling to room temperature, the curls are stripped off while retaining the shape and hung up on a frame made specially for this purposes and the curl length ($L_0$) is measured in cm on the attached scale.

To determine a curl retention value, 5 hair curls should be used. The curls are hung in a climatically controlled chamber at 20° C. and 75% or 90% relative atmospheric humidity. After 5 hours, the length (Lt) is read off.

The curl retention is calculated as follows:

$$\text{Curl retention in \%} = \frac{L - L_t}{L - L_0} * 100$$

L=length of the hair (15.5 cm)
$L_0$=length of the hair curl after drying
$L_t$=length of the hair curl after climate treatment The curl retention quoted is the average of the 5 individual measurements after 5 h at 20° C. and 75% and 90% relative humidity.

Flexural Rigidity:

The dry, weighed tresses are immersed three times into demin. water, stripped, pressed between filter paper and weighed. The tresses are then immersed three times into the polymer solution to be tested (formulation without propellant gas), stripped off using the fingers as they are pulled out and likewise pressed between filter paper and weighed. The tress is then shaped by hand such that the cross section is as round as possible. The tress is hung up overnight freely suspended by a clamp in a climatically controlled room (21° C. and 65% relative humidity).

The tests are carried out in a climatically controlled room at 21° C. and 65% relative atmospheric humidity using a tensile/pressure testing instrument (model Easytest 86 802, Frank). The hair tress is placed symmetrically on two cylindrical rolls (diameter 4 mm, distance apart 90 mm) of the sample holder. The tress is then bent from above in the middle by 40 mm using a rounded punch (breakage of the polymer film). The force required for this is measured using a load cell (50 N or 10 N) and is given in Newtons. Each polymer solution is tested on 5 different hair tresses.

The result used is the average of the 5 individual measurements.

The determinations of the K value, of the pH, the curl retention and the flexural rigidity were carried out for the formulations listed in Table 2.

TABLE 2

| Foam formulation | Polymer from Example | pH | VP [% by wt.] | MAM [% by wt.] | VI [% by wt.] | QVI [% by wt.] | K value | Setting [cN] | Curl retention [%] |
|---|---|---|---|---|---|---|---|---|---|
| SF1* | S1 | 7.6 | 55 | 35 | 10 | — | 92 | 356 | 95 |
| SF2 | S1 | 5.4 | 55 | 35 | 10 | — | 92 | 465 | 97 |
| SF3* | S6 | 6.7 | 55 | 35 | 10 | | 86.2 | 323 | 99 |
| SF4 | S6 | 5.5 | 55 | 35 | 10 | — | 86.2 | 378 | 99 |
| SF6* | S2 | 7.4 | 60 | 30 | 5 | 5 | 92.8 | 388 | 92 |
| SF7 | S2 | 5.6 | 60 | 30 | 5 | 5 | 92.8 | 430 | 92 |
| SF8* | S4 | 7.4 | 55 | 35 | 5 | 5 | 97.5 | 349 | 95 |
| SF9 | S4 | 5.7 | 55 | 35 | 5 | 5 | 97.5 | 427 | 95 |
| SF10* | S3 | 6.1 | 55 | 35 | 5 | 5 | 86.8 | 256 | 94 |
| SF11 | S7 | 5.6 | 55 | 35 | 5 | 5 | 103.7 | 376 | 99 |
| SF12 | S8 | 5.8 | 55 | 29 | 8 | 8 | 102.9 | 411 | 96 |
| SF13* | S9 | 6.7 | 55 | 29 | 10 | 6 | 95.9 | 480 | 94 |
| SF14 | S9 | 5.5 | 55 | 29 | 10 | 6 | 95.9 | 550 | 97 |
| SF15* | S10 | 7.1 | 55 | 29 | 10 | 6 | 99.9 | 348 | — |
| SF16 | S10 | 5.5 | 55 | 29 | 10 | 6 | 99.9 | 406 | — |

| Foam formulation | Polymer from Example | pH | VP [% by wt.] | MAM [% by wt.] | DMAPMAM [% by wt.] | K value | Setting [cN] | Stickiness |
|---|---|---|---|---|---|---|---|---|
| SF17* | S11 | 6.9 | 55 | 35 | 10 | 94.7 | 285 | slightly sticky |
| SF18 | S11 | 5.6 | 55 | 35 | 10 | 94.7 | 320 | not sticky |

*Comparative experiments

| PF1 to PF11) Pump spray | | | |
|---|---|---|---|
| Ingredient | % by wt. | CTFA name | Manufacturer |
| 20% strength by weight aqueous solution of one of the polymers from S1 to S11 | 10.0 | | |
| Chitosan (2% strength by weight aqueous solution, adjusted to pH 6 with lactic acid) | 50.0 | | Sigma-Aldrich |
| Water, distilled | 44.0 | Aqua | |

Moreover, preservatives, soluble ethoxylated silicone, perfume oil and further cosmetic customary ingredients may be added to the preparations.

Preparation: All of the components are weighed, homogenized slowly at room temperature with stirring and the pH is adjusted to a value of from pH 5 to pH 6 with lactic acid or phosphoric acid.

| GF1 to GF11) Setting gel 1 | | | |
|---|---|---|---|
| Ingredient | % by wt. | CTFA name | Manufacturer |
| 20% by weight aqueous solution of one of the polymers from S1 to S11 | 10.0 | | |
| Glycerol | 2.0 | | |
| Natrosol ® 250 HR (2% strength by weight aqueous solution) | 50.0 | Hydroxyethyl-cellulose | Hercules |
| Lactic acid or phosphoric acid | until pH in the range from 5 to 6 | | |
| Water, distilled | ad 100 | Aqua | |

Moreover, preservatives, soluble ethoxylated silicone, perfume oil and further cosmetically customary ingredients may be added to the preparations.

Preparation: All components are weighed, homogenized slowly at room temperature with stirring and the pH is adjusted to a value of pH 5 to pH 6 with lactic acid or phosphoric acid.

| GF12 to GF22) Setting gel 2 | | | |
|---|---|---|---|
| Ingredient | % by wt. | CTFA name | Manufacturer |
| 20% strength by weight aqueous | 5 | | |

GF12 to GF22) Setting gel 2

| Ingredient | % by wt. | CTFA name | Manufacturer |
|---|---|---|---|
| solution of one of the polymers from S1 to S11 | | | |
| Natrosol ® 250 HR | 2.0 | Hydroxyethyl-cellulose | Hercules |
| D-Panthenol USP | 0.5 | Panthenol | BASF |
| Karion F liquid | 1.0 | Sorbitol | |
| Lactic acid or phosphoric acid | until pH in the range from 5 to 6 | | |
| Water, dist. | ad 100.0 | Aqua | |

Moreover, preservatives, soluble ethoxylated silicone, perfume oil and further cosmetic customary ingredients may be added to the preparations.

Preparation: All components are weighed and homogenized slowly at room temperature with stirring.

HS1 to HS11) Aqueous handpump sprays

| Ingredient | % by wt. | CTFA name | Manufacturer |
|---|---|---|---|
| 20% strength by weight aqueous solution of one of the polymers from S1 to S11 | 7.5 | | |
| Luviskol ®VA64 (30% strength water/ethanol solution) | 5.0 | VP/VA Copolymer | BASF |
| Glycerol | 3.0 | | |
| Lactic acid or phosphoric acid | until pH is in the range from 5 to 6 | | |
| Water, dist. | ad 100.0 | Aqua | |

Moreover, preservatives, soluble ethoxylated silicone, perfume oil and further cosmetic customary ingredients may be added to the preparations.

Preparation: All components are weighed and homogenized slowly at room temperature with stirring.

SF19 to SF29) Setting foam 1

| Ingredient | % by wt. | CTFA name | Manufacturer |
|---|---|---|---|
| 20% strength by weight aqueous solution of one of the polymers from S1 to S11 | 7.5 | | |
| Cremophor ® A 25 | 0.2 | Ceteareth 25 | BASF |
| Comperlan ® KD | 0.1 | Coamide DEA | Henkel |
| Dimethyl ether | 10.0 | | |
| Lactic acid or phosphoric acid | until pH is in the range from 5 to 6 | | |
| Water, dist. | ad 100.0 | Aqua | |

Moreover, preservatives, soluble ethoxylated silicone, perfume oil and further cosmetic customary ingredients may be added to the preparations.

Preparation: The components are weighed and homogenized slowly at room temperature with stirring. The preparation is then bottled and the propellant gas is added.

SF30 to SF40) Setting foam 2

| Ingredient | % by wt. | CTFA name | Manufacturer |
|---|---|---|---|
| 20% strength by weight aqueous solution of one of the polymers from S1 to S11 | 15.0 | | |
| Cremophor ® A 25 | 0.2 | Ceteareth 25 | BASF |
| Comperlan ® KD | 0.1 | Coamide DEA | Henkel |
| Dimethyl ether | 10.0 | | |
| Lactic acid or phosphoric acid | until pH is in the range from 5 to 6 | | |
| Water, dist. | ad 100.0 | Aqua | |

Moreover, preservatives, soluble ethoxylated silicone, perfume oil and further cosmetic customary ingredients may be added to the preparations.

Preparation: The components are weighed and homogenized slowly at room temperature with stirring. The preparation is then bottled and the propellant gas is added.

SF41 to SF51) Setting foam 3

| Ingredient | % by wt. | CTFA name | Manufacturer |
|---|---|---|---|
| 20% strength by weight aqueous solution of one of the polymers from S1 to S11 | 15.0 | | |
| Luviquat ® Mono LS | 2.00 | Cocotrimonium Methosulfate | BASF |
| D-Panthenol USP | 1.0 | Panthenol | BASF |
| Propane/butane | 10.0 (to 3.5 bar) | Propane/Butane | |
| Lactic acid or phosphoric acid | until pH is in the range from 5 to 6 | | |
| Water, dist. | ad 100.0 | Aqua | |

Moreover, preservatives, soluble ethoxylated silicone, perfume oil and further cosmetic customary ingredients may be added to the preparations.

Preparation: The components are weighed and homogenized slowly at room temperature with stirring. The preparation is then bottled and the propellant gas is added.

CS1 to CS11) Conditioner shampoo 1

| Ingredient | % by wt. | CTFA name | Manufacturer |
|---|---|---|---|
| Phase A | | | |
| Texapon ® NSO 28% strength | 50.0 | Sodium Laureth Sulphate | Henkel |
| Comperlan ® KD | 1.0 | Coamide DEA | Henkel |

-continued

| CS1 to CS11) Conditioner shampoo 1 | | | |
|---|---|---|---|
| Ingredient | % by wt. | CTFA name | Manufacturer |
| 20% strength by weight aqueous solution of one of the polymers from S1 to S11 | 4.5 | | |
| Lactic acid or phosphoric acid | until pH is in the range from 5 to 6 | | |
| Water, dist. | 15.5 | Aqua | |
| Perfume oil | q.s. | | |
| Phase B | | | |
| Water, dist. | 27.5 | Aqua | |
| Sodium chloride | 1.5 | Sodium Chloride | |
| Preservative | q.s | | |

Moreover, preservatives, soluble ethoxylated silicone, perfume oil and further cosmetic customary ingredients may be added to the preparations.

Weigh in and dissolve phases A and B separately with stirring. Adjust phase A to a pH of 5 to 6 with lactic acid (20% by weight in water) and make up to 100% by weight with water. Phase B is slowly stirred into phase A.

| CS12 to CS22) Conditioner shampoo 2 | | | |
|---|---|---|---|
| Ingredient | % by wt. | CTFA name | Manufacturer |
| Phase A | | | |
| Tego Betain ® L 7 | 15.00 | Cocamidopropyl Betaine | Degussa |
| Amphotensid ® GB 2009 | 10.00 | Disodium Cocoampho-diacetate | Zschimmer & Schwarz |
| Cremophor ® PS 20 | 5.00 | Polysorbate 20 | BASF |
| Plantacare ® 2000 | 5.00 | Decyl Glucoside | Cognis |
| 20% strength by weight aqueous solution of one of the polymers from S1 to S11 | 0.5 to 5.0 | | |
| Guar hydroxypropyl-trimonium chloride | 0.15 | | |
| Rewopal ® LA 3 | 2.00 | Laureth-3 | Degussa |
| Lactic acid or phosphoric acid | until pH is in the range from 5 to 6 | | |
| Water, demineralized | ad 100 | Aqua dem | |
| Perfume oil | q.s. | | |
| Preservative | q.s. | | |
| Phase B | | | |
| Stepan ® PEG 6000 DS | 3.00 | PEG-150 Distearate | Stepan Co. |

Weigh in and dissolve phases A and B separately with stirring. Adjust phase A to a pH of from 5 to 6 with lactic acid (20% by weight in water) and make up to 100% by weight with water. Phase B is slowly stirred into phase A.

| CS23 to CS33) Conditioner shampoo 3 | | | |
|---|---|---|---|
| Ingredient | % by wt. | CTFA name | Manufacturer |
| Texapon ® NSO 28% strength | 30.0 | Sodium Laureth Sulphate | Henkel |
| Dehyton ® G | 6.00 | Sodium Cocoamphoacetate | Henkel |
| Dehyton ® K | 6.00 | Cocamidopropyl Betaine | Henkel |
| Euperlan ® PK 771 | 3.00 | Sodium Laureth Sulfate, Glycol Distearate, Cocamide MEA, Laureth-10 | Henkel |
| 20% strength by weight aqueous solution of one of the polymers from S1 to S11 | 0.5 to 5.0 | | |
| Luviquat ® Care | 7.70 | Polyquaternium-44 | BASF |
| Amodimethicone | 2.00 | Amodimethicone | |
| Sodium chloride | 1.00 | Sodium Chloride | |
| Lactic acid or phosphoric acid | until pH is in the range from 5 to 6 | | |
| Water, demineralized | ad 100 | Aqua dem | |

Moreover, preservatives, soluble ethoxylated silicone, perfume oil and further cosmetic customary ingredients may be added to the preparations.

Preparation: The components are weighed, homogenized slowly at room temperature with stirring, the pH is adjusted to a value of from pH 5 to pH 6 with lactic acid or phosphoric acid and made up to 100% by weight with water.

| CM1 to CM11) Conditioner mousse 1 | | | |
|---|---|---|---|
| Ingredient | % by wt. | CTFA name | Manufacturer |
| Luviquat ® PQ 11 | 10.00 | Polyquaternium-11 | BASF |
| 20% strength by weight aqueous solution of one of the polymers from S1 to S11 | 0.5-5.0 | | |
| Luviquat ® Mono CP | 0.50 | Hydroxyethyl Cetyldimonium Phosphate | BASF |
| D-Panthenol ® USP | 1.00 | Panthenol | BASF |
| Lactic acid or phosphoric acid | until pH is in the range from 5 to 6 | | |
| Water, demineralized | ad 100 | Aqua dem | |
| Propane/butane | 6.00 | Propane/Butane | |

Moreover, preservatives, soluble ethoxylated silicone, perfume oil and further cosmetic customary ingredients may be added to the preparations.

Preparation: The components are weighed, homogenized slowly at room temperature with stirring, the pH is adjusted to a value of from pH 5 to pH 6 with lactic acid or phosphoric acid and made up to 100% by weight with water. The preparation is then bottled and the propellant gas is added.

| CM12 to CM22) Conditioner mousse 2 | | | |
|---|---|---|---|
| Ingredient | % by wt. | CTFA name | Manufacturer |
| Polyquaternium-4 | 1.00 | | |
| 20% strength by weight aqueous solution of one of the polymers from S1 to S11 | 4.0-10.00 | | |
| Luviquat ® Mono CP | 0.50 | Hydroxyethyl Cetyldimonium Phosphate | BASF |
| Lactic acid or phosphoric acid | until pH is in the range from 5 to 6 | | |
| Water, demineralized | ad 100 | Aqua dem | |
| Propane/butane | 6.00 | Propane/Butane | |

Moreover, preservatives, soluble ethoxylated silicone, perfume oil and further cosmetic customary ingredients may be added to the preparations.

Preparation: The components are weighed, homogenized slowly at room temperature with stirring, the pH is adjusted to a value of from pH 5 to pH 6 with lactic acid or phosphoric acid and made up to 100% by weight with water. The preparation is then bottled and the propellant gas is added.

| SM1 to SM11) Styling mousse 1 | | | |
|---|---|---|---|
| Ingredient | % by wt. | CTFA name | Manufacturer |
| Phase A | | | |
| Luviquat ® Mono LS | 2.00 | Cocotrimonium Methosulfate | BASF |
| Phase B | | | |
| Luviflex ® Soft | 6.70 | Acrylates Copolymer | BASF |
| AMP | 0.60 | Aminomethyl Propanol | Angus Chemical Company |
| 20% strength by weight aqueous solution of one of the polymers from S1 to S11 | 5.0-10.0 | | |
| Dimethicone copolyol | 0.50 | Dimethicone Copolyol | |
| Cremophor ® A 25 | 0.20 | Ceteareth-25 | BASF |
| D-Panthenol ® USP | 0.20 | Panthenol | BASF |
| Uvinul ® P 25 | 0.10 | PEG-25 PABA | BASF |
| Natrosol ® 250 HR | 0.20 | Hydroxyethyl-cellulose | Aqualon GmbH |
| Lactic acid or phosphoric acid | until pH is in the range from 5 to 6 | | |
| Water, demineralized | ad 100 | Aqua dem | |
| Phase C | | | |
| Dymel HFC 152a | 10.00 | Hydrofluoro-carbon 152a | Dupont |

Preparation: The components for phases A and B are weighed, homogenized slowly at room temperature with stirring, the pH of phase B is adjusted to a value of from pH 5 to pH 6 with lactic acid, or phosphoric acda and phase B is made up to 100% by weight with water. A and B are then mixed, the preparation is bottled and the propellant gas (phase C) is added.

| SM12 to SM22) Styling mousse 2 | | | |
|---|---|---|---|
| Ingredient | % by wt. | CTFA name | Manufacturer |
| Phase A | | | |
| Luviquat ® Mono LS | 2.00 | Cocotrimonium Methosulfate | BASF |
| Phase B | | | |
| Luviquat ® Care | 7.70 | Polyquaternium-44 | BASF |
| 20% strength by weight aqueous solution of one of the polymers from S1 to S11 | 5.0-10.0 | | |
| Lactic acid or phosphoric acid | until pH is in the range from 5 to 6 | | |
| Water, demineralized | ad 100 | Aqua dem | |
| Phase C | | | |
| Propane/butane | 10.00 | | |

Preparation: The components for phases A and B are weighed, slowly homogenized at room temperature with stirring, the pH of phase B is adjusted to a value of from pH 5 to pH 6 with lactic acid or phosphoric acid and phase B is made up to 100% by weight with water. A and B are then mixed, the preparation is bottled and the propellant gas (phase C) is added.

| SM23 to SM33) Styling mousse 3 | | | |
|---|---|---|---|
| Ingredient | % by wt. | CTFA name | Manufacturer |
| Phase A | | | |
| Luviquat ® Mono LS | 2.00 | Cocotrimonium Methosulfate | BASF |
| Phase B | | | |
| Styleze ® 2000 | 2.00 | VP/Acrylates/Lauryl Methacrylate Copolymer | ISP |
| AMP | 0.53 | | |
| 20% strength by weight aqueous solution of one of the polymers from S1 to S11 | 0.5-5 | | |
| Cremophor ® A 25 | 0.20 | Ceteareth-25 | BASF |
| D-Panthenol USP ® | 0.50 | Panthenol | BASF |
| Uvinul ® MS 40 | 0.05 | Benzophenone-4 | BASF |
| Dow Corning 949 ® cationic emulsion | 0.20 | Amodimethicone/Cetrimonium Chloride/Trideceth-12 | Dow Corning |
| Ethanol 96% | 15.00 | Alcohol | |
| Lactic acid or phosphoric acid | until pH is in the range from 5 to 6 | | |
| Water, demineralized | ad 100 | Aqua dem | |
| Phase C | | | |
| Natrosol ® 250 HR | 0.20 | Hydroxyethyl-cellulose | Aqualon GmbH |

SM23 to SM33) Styling mousse 3

| Ingredient | % by wt. | CTFA name | Manufacturer |
|---|---|---|---|
| Phase D | | | |
| Propane/butane | 6.00 | Propane/Butane | |

Preparation: The components for phases A and B are weighed, homogenized slowly at room temperature with stirring, the pH of phase B is adjusted to a value of from pH 5 to pH 6 with lactic acid or phosphoric acid and phase B is made up to 100% by weight with water. A and B are then mixed, phase C is added, the preparation is bottled and the propellant gas (phase D) is added.

SM34 to SM44) Styling mousse 4

| Ingredient | % by wt. | CTFA name | Manufacturer |
|---|---|---|---|
| Phase A | | | |
| Cetrimonium chloride | 2.00 | Cetrimonium chloride | |
| Phase B | | | |
| Luviquat ® Hold | 7.00 | Polyquaternium-46 | BASF |
| 20% strength by weight aqueous solution of one of the polymers from S1 to S11 | 0.5-5 | | |
| Cremophor ® A 25 | 0.20 | Ceteareth-25 | BASF |
| D-Panthenol USP ® | 0.50 | Panthenol | BASF |
| Uvinul ® MS 40 | 0.05 | Benzophenone-4 | BASF |
| Dow Corning 949 ® Cationic | 0.20 | | Dow Corning |
| Ethanol 96% | 15.00 | Alcohol | |
| Lactic acid or phosphoric acid | until pH is in the range from 5 to 6 | | |
| Water, demineralized | ad 100 | Aqua dem | |
| Phase C | | | |
| Natrosol ® 250 HR | 0.20 | Hydroxyethyl-cellulose | Aqualon GmbH |
| Phase D | | | |
| Propane/butane | 6.00 | Propane/Butane | |

Preparation: The components for phases A and B are weighed, slowly homogenized at room temperature with stirring, the pH of phase B is adjusted to a value of from pH 5 to pH 6 with lactic acid or phosphoric acid and phase B is made up to 100% by weight with water. A and B are then mixed, phase C is added, the preparation is bottled and the propellant gas (phase D) is added.

SM45 to SM55) Styling mousse 5

| Ingredient | % by wt. | CTFA name | Manufacturer |
|---|---|---|---|
| Phase A | | | |
| Cremophor ® RH 40 | q.s. | PEG-40 Hydrogenated Castor Oil | BASF |
| Water, demineralized | ad 100 | Aqua dem | |
| Phase B | | | |
| Flexan ® 130 | 7.00 | Sodium Polystyrene Sulfonate | National Starch |
| 20% strength by weight aqueous solution of one of the polymers from S1 to S11 | 5.0-10.0 | | |
| Cetrimonium bromide | 0.50 | Cetrimonium Bromide | |
| Lactic acid or phosphoric acid | until pH is in the range from 5 to 6 | | |
| Phase C | | | |
| Propane/butane | 6.00 | Propane/Butane | |

Preparation: Weigh and dissolve phases A and B separately with stirring and mix. Adjust phase B to a pH of from pH 5 to pH 6 with lactic acid or phosphoric acid, if appropriate add further substances such as preservative or perfume oil to phase A or B. Bottle and add propellant gas (phase C).

SM56 to SM66) Styling mousse 6

| Ingredient | % by wt. | CTFA name | Manufacturer |
|---|---|---|---|
| Phase A | | | |
| Cremophor ® RH 40 | q.s. | PEG-40 Hydrogenated Castor Oil | BASF |
| Water, demineralized | ad 100 | Aqua dem | |
| Phase B | | | |
| UCare polymer | 0.5 | Polyquaternium-10 | Amerchol |
| 20% strength by weight aqueous solution of one of the polymers from S1 to S11 | 5.0-10.0 | | |
| Cetrimonium bromide | 0.50 | | |
| Lactic acid or phosphoric acid | until pH is in the range from 5 to 6 | | |
| Phase C | | | |
| Propane/butane | 6.00 | Propane/Butane | |

Preparation: Weigh and dissolve phases A and B separately with stirring and mix. Adjust phase B to a pH of from pH 5 to pH 6 with lactic acid or phosphoric acid, if appropriate add further substances such as preservative or perfume oil to phase A or phase B. Bottle and add propellant gas (phase C).

SM67 to SM77) Styling mousse 7

| Ingredient | % by wt. | CTFA name | Manufacturer |
|---|---|---|---|
| Phase A | | | |
| Cremophor ® RH 40 | q.s. | PEG-40 Hydrogenated Castor Oil | BASF |
| Water, demineralized | ad 100 | Aqua dem | |
| Phase B | | | |
| Luviquat ® HM 552 | 10.00 | Polyquaternium-16 | BASF |
| 20% strength by weight aqueous solution of one of the polymers from S1 to S11 | 0.5-5.0 | | |
| Luviquat ® Mono CP | 0.50 | Hydroxyethyl Cetyldimonium Phosphate | BASF |
| Lactic acid or phosphoric acid | until pH is in the range from 5 to 6 | | |
| Phase C | | | |
| Propane/butane | 6.00 | Propane/Butane | |

Preparation: Weigh and dissolve phases A and B separately with stirring and mix. Adjust phase B to a pH of from pH 5 to pH 6 with lactic acid or phosphoric acid, if appropriate add further substances such as preservative or perfume oil to phase A or phase B. Bottle and add propellant gas (phase C).

SM78 to SM88) Styling mousse 8

| Ingredient | % by wt. | CTFA name | Manufacturer |
|---|---|---|---|
| Phase A | | | |
| Luviquat ® Mono LS | 2.00 | Cocotrimonium Methosulfate | BASF |
| Phase B | | | |
| Hydagen HCMF | 2.00 | Chitosan | Cognis |
| 20% strength by weight aqueous solution of one of the polymers from S1 to S11 | 0.5-5.0 | | |
| Dimethicone copolyol | 0.50 | Dimethicone Copolyol | |
| Cremophor ® A 25 | 0.20 | Ceteareth-25 | BASF |
| D-Panthenol USP ® | 0.20 | Panthenol | BASF |
| Uvinul ® P 25 | 0.10 | G-25 PABA | BASF |
| Lactic acid or phosphoric acid | until pH is in the range from 5 to 6 | | |
| Water, demineralized | ad 100 | Aqua dem | |
| Phase C | | | |
| HFC 152 A | 10.00 | | |

Preparation: Weigh and dissolve phases A and B separately with stirring and mix. Adjust phase B to a pH of from pH 5 to pH 6 with lactic acid or phosphoric acid, if appropriate add further substances such as preservative or perfume oil to phase A or B. Bottle and add propellant gas (phase C).

SM89 to SM99) Styling mousse 9

| Ingredient | % by wt. | CTFA name | Manufacturer |
|---|---|---|---|
| Luviskol ® VA 64 W | 10.00 | PVP/VA Copolymer | BASF |
| 20% strength by weight aqueous solution of one of the polymers from S1 to S11 | 2.0-5.0 | | |
| Luviquat ® Mono CP | 0.20 | Hydroxyethyl Cetyldimonium Phosphate | BASF |
| Dimethicone copolyol | 0.50 | Dimethicone Copolyol | |
| Cremophor ® A 25 | 0.20 | Ceteareth-25 | BASF |
| Ethanol | 10.00 | Alcohol | |
| Lactic acid or phosphoric acid | until pH is in the range from 5 to 6 | | |
| Water, demineralized | ad 100 | Aqua dem | |
| Propane/butane | 10.00 | Propane/Butane | |

Preparation: Weigh components and dissolve with stirring and mix. Use lactic acid or phosphoric acid to adjust to a pH of from pH 5 to pH 6, if appropriate add further substances such as preservative or perfume oil. Bottle and add propellant gas.

Use in skin cosmetics:

C1 to C11) Standard O/W cream

| Ingredient | % by wt. | CTFA name | Manufacturer |
|---|---|---|---|
| Oil phase | | | |
| Cremophor ® A6 | 3.5 | Ceteareth-6 (and) Stearyl Alcohol | BASF |
| Cremophor ® A25 | 3.5 | Ceteareth-25 | BASF |
| Glycerol monostearate s.e. | 2.5 | Glyceryl Stearate | |
| Paraffin oil | 7.5 | Paraffin Oil | |
| Cetyl alcohol | 2.5 | Cetyl Alcohol | |
| Luvitol ® EHO | 3.2 | Cetearyl Octanoate | BASF |
| Vitamin E acetate | 1.0 | Tocopheryl Acetate | |
| Nip-Nip | 0.1 | Methyl and Propyl 4-hydroxybenzoate (7:3) | |
| Water phase | | | |
| Water, demineralized | ad 50 | Aqua dem | |
| 20% strength by weight aqueous solution of one of the polymers from S1 to S11 | 2.0-8.0 | | |
| 1,2-propylene glycol care | 1.5 | Propylene Glycol | |
| Germall II | 0.1 | Imidazolidinyl-Urea | |
| Lactic acid or phosphoric acid | until pH is in the range from 5 to 6 | | |

Preparation: Weigh and homogenize, with stirring, the oil phases and water phase separately at a temperature of about 80° C., adjust the aqueous phase to a pH of from pH 5 to pH 6 with lactic acid or phosphoric acid. Slowly stir water phase into oil phase. Cool slowly to RT with stirring.

| T1 to T11 Day lotion | | | |
|---|---|---|---|
| Ingredient | % by wt. | CTFA name | Manufacturer |
| Oil phase | | | |
| Cremophor ® A6 | 1.5 | Ceteareth-6 (and) Stearyl Alcohol | BASF |
| Cremophor ® A25 | 1.5 | Ceteareth-25 | BASF |
| Glycerol monostearate s.e. | 5.0 | Glyceryl Stearate | |
| Uvinul ® MS 40 | 0.5 | Benzophenone-4 | BASF |
| Paraffin oil | 3.5 | Paraffin Oil | |
| Cetyl alcohol | 0.5 | Cetyl Alcohol | |
| Luvitol ® EHO | 10.0 | Cetearyl Octanoate | BASF |
| D-Panthenol 50 P ® | 3.0 | Panthenol and Propylene glycol | |
| Vitamin E acetate | 1.0 | Tocopheryl Acetate | |
| Tegiloxan ® 100 | 0.3 | Dimethicone | |
| Nip-Nip | 0.1 | Methyl and Propyl 4-hydroxybenzoate (7:3) | |
| Water phase | | | |
| 20% strength by weight aqueous solution of one of the polymers from S1 to S11 | 2.5-5.0 | | |
| 1,2-propylene glycol | 1.5 | Propylene Glycol | |
| Germall II | | Imidazolidinyl-Urea | |
| Lactic acid or phosphoric acid | until pH is in the range from 5 to 6 | | |
| Water, demineralized | ad 50 | Aqua dem | |

Preparation: Weigh and homogenize, with stirring, the oil phases and water phase separately at a temperature of about 80° C. Adjust water phase to a pH of from pH 5 to pH 6 with lactic acid or phosphoric acid and stir slowly into oil phase. Cool slowly to RT with stirring.

We claim:

1. An aqueous hair preparation comprising:
   A) 2 to 20% by weight of at least one water-soluble or water-dispersible copolymer A) with cationogenic groups, which consists essentially of:
      a) 3 to 15% by weight of N-vinylimidazole,
      b1) 30 to 70% by weight of N-vinylpyrrolidone,
      b2) 20 to 35% by weight of methacrylamide, and
      b3) at least one monomer b3) which is a quaternization product of N-vinylimidazole, whereby the amount of monomer b3) is at most 10% by weight, in copolymerized form;
   with the proviso that the sum of the amounts of components a) to b3) is 100% by weight; and
   B) at least one cosmetically acceptable carrier,
   wherein the pH of the aqueous preparation has a value in the range from pH 4 to pH 6.

2. The aqueous hair preparation according to claim 1, wherein the component B) is selected from the group consisting of:
   i water;
   ii water-miscible organic solvents;
   iii oils, fats, and waxes;
   iv esters of $C_6$-$C_{30}$-monocarboxylic acids with mono-, di- or trihydric alcohols which are different from iii);
   v saturated acyclic and cyclic hydrocarbons;
   vi fatty acids;
   vii fatty alcohols;
   viii propellant gases;
   and mixtures thereof.

3. The aqueous hair preparation according to claim 1, further comprising at least one additive different from components A) and B), wherein the additive is selected from the group consisting of cosmetically active ingredients, emulsifiers, surfactants, preservatives, perfume oils, thickeners, hair polymers, hair and skin conditioners, graft polymers, water-soluble or dispersible silicone-containing polymers, light protection agents, bleaches, gel formers, care agents, colorants, tinting agents, tanning agents, dyes, pigments, consistency-imparting agents, humectants, refatting agents, collagen, protein hydrolyzates, lipids, antioxidants, antifoams, antistats, emollients and softeners.

4. The aqueous hair preparation according to claim 1, further comprising at least one additional water-soluble polymer.

5. The aqueous hair preparation according to claim 4, wherein the additional water-soluble polymer is chitosan and/or a chitosan derivative.

6. The aqueous hair preparation according to claim 1, further comprising at least one non-ionic thickener.

7. The aqueous hair preparation according to claim 1, wherein the pH has a value in the range from pH 5 to pH 6.

8. The aqueous hair preparation according to claim 1, wherein the pH is adjusted by adding hydroxycarboxylic acid.

9. The aqueous hair preparation according to claim 1, wherein the pH is adjusted by adding inorganic acid.

10. A method of preparing an aqueous hair preparation according to claim 1, comprising:
    adding the at least one water-soluble or water-dispersible copolymer A) to at least one cosmetically acceptable carrier B),
    wherein the pH adjustment takes place after the preparation of copolymer A) is complete.

11. A cosmetic composition comprising the aqueous hair preparation of claim 1, wherein the cosmetic composition is a skin-cleansing composition, a composition for the care and protection of skin, a nailcare composition, a preparation for decorative cosmetics or a hair-treatment composition.

12. A setting agent or conditioner comprising the aqueous hair preparation according to claim 1.

13. The composition according to claim 11, in the form of a hair gel, shampoo, setting foam, hair tonic, hairspray or hair foam.

14. The aqueous hair preparation according to claim 1, wherein the pH has a value of from 4.5 to 6.

15. A foam comprising the aqueous hair preparation according to claim 1.

16. A mousse comprising the aqueous hair preparation according to claim 1.

* * * * *